US008067491B2

(12) United States Patent
Cruse et al.

(10) Patent No.: US 8,067,491 B2
(45) Date of Patent: *Nov. 29, 2011

(54) SILATED CYCLIC CORE POLYSULFIDES, THEIR PREPARATION AND USE IN FILLED ELASTOMER COMPOSITIONS (75) Inventors: Richard W. Cruse, Yorktown Heights, NY (US); W. Michael York, Concord, NC (US); Eric R. Pohl, Mt. Kisco, NY (US); Antonio Chaves, Chappaqua, NY (US); Prashant Joshi, Gaitherburg, MD (US)

(73) Assignee: Momentive Performance Materials Inc., Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/706,193

(22) Filed: Feb. 16, 2010

(65) Prior Publication Data
US 2010/0174019 A1 Jul. 8, 2010

Related U.S. Application Data (63) Continuation of application No. 11/647,901, filed on Dec. 28, 2006, now Pat. No. 7,687,558.

(51) Int. Cl.
B60C 1/00 (2006.01)
C08K 5/24 (2006.01)
C08K 3/34 (2006.01)
C08K 3/04 (2006.01)

(52) U.S. Cl. ......... 524/262; 524/261; 524/492; 524/495
(58) Field of Classification Search .................. 524/261, 524/262, 571, 492, 495
See application file for complete search history.

(56) References Cited

U.S. PATENT DOCUMENTS

| 3,505,166 | A | 4/1970 | Jones et al. |
|---|---|---|---|
| 3,624,160 | A | 11/1971 | Jones et al. |
| 3,692,812 | A | 9/1972 | Berger |
| 3,798,196 | A | 3/1974 | Rocktaschel et al. |
| 3,842,111 | A | 10/1974 | Meyer-Simon et al. |
| 3,869,340 | A | 3/1975 | Kotzsch et al. |
| 3,873,489 | A | 3/1975 | Thurn et al. |
| 3,922,436 | A | 11/1975 | Bell et al. |
| 3,946,059 | A | 3/1976 | Janssen et al. |
| 3,957,718 | A | 5/1976 | Pochert et al. |
| 3,978,103 | A | 8/1976 | Meyer-Simon et al. |
| 3,997,356 | A | 12/1976 | Thurn et al. |
| 3,997,581 | A | 12/1976 | Pletka et al. |
| 4,044,037 | A | 8/1977 | Mui et al. |
| 4,060,539 | A | 11/1977 | Seiler et al. |
| 4,072,701 | A | 2/1978 | Pletka et al. |
| 4,076,550 | A | 2/1978 | Thurn et al. |
| 4,099,981 | A | 7/1978 | Mui et al. |
| 4,100,172 | A | 7/1978 | Mui et al. |
| 4,113,696 | A | 9/1978 | Williams et al. |
| 4,125,552 | A | 11/1978 | Speier |
| 4,128,438 | A | 12/1978 | Wolff et al. |
| 4,129,585 | A | 12/1978 | Buder et al. |
| 4,152,347 | A | 5/1979 | Pletka |
| 4,184,998 | A | 1/1980 | Shippy et al. |
| 4,210,459 | A | 7/1980 | Williams et al. |
| 4,222,915 | A | 9/1980 | Wolfff et al. |
| 4,229,333 | A | 10/1980 | Wolff et al. |
| 4,375,988 | A | 3/1983 | Mueller et al. |
| 4,384,132 | A | 5/1983 | Schwarz et al. |
| 4,408,064 | A | 10/1983 | Schwarz et al. |
| 4,444,936 | A | 4/1984 | Schwarz et al. |
| 4,507,490 | A | 3/1985 | Panster et al. |
| 4,514,231 | A | 4/1985 | Kerner et al. |
| 4,517,336 | A | 5/1985 | Wolff et al. |
| 4,519,430 | A | 5/1985 | Ahmad et al. |
| 4,524,169 | A | 6/1985 | Wolff et al. |
| 4,574,133 | A | 3/1986 | Umpleby |
| 4,704,414 | A | 11/1987 | Kerner et al. |
| 4,709,065 | A | 11/1987 | Yoshioka et al. |
| 4,820,751 | A | 4/1989 | Takeshita et al. |
| 4,959,153 | A | 9/1990 | Bradshaw et al. |
| 4,981,937 | A | 1/1991 | Kuriyama et al. |
| 5,037,872 | A | 8/1991 | Schwarze et al. |
| 5,110,969 | A | 5/1992 | Dittrich et al. |
| 5,116,886 | A | 5/1992 | Wolff et al. |
| 5,159,009 | A | 10/1992 | Wolff et al. |
| 5,399,739 | A | 3/1995 | French et al. |
| 5,401,789 | A | 3/1995 | Wolff et al. |
| 5,405,985 | A | 4/1995 | Parker et al. |
| 5,466,848 | A | 11/1995 | Childress |
| 5,468,893 | A | 11/1995 | Parker et al. |
| 5,489,701 | A | 2/1996 | Childress et al. |
| 5,596,116 | A | 1/1997 | Childress et al. |
| 5,605,951 | A | 2/1997 | Sandstrom et al. |
| 5,650,457 | A | 7/1997 | Scholl et al. |
| 5,663,226 | A | 9/1997 | Scholl et al. |
| 5,663,358 | A | 9/1997 | Cohen et al. |
| 5,663,395 | A | 9/1997 | Gobel et al. |
| 5,663,396 | A | 9/1997 | Musleve et al. |
| 5,672,639 | A | 9/1997 | Corvasce et al. |
| 5,674,932 | A | 10/1997 | Agostini et al. |
| 5,675,014 | A | 10/1997 | Cohen et al. |
| 5,679,728 | A | 10/1997 | Kawazura et al. |
| 5,684,172 | A | 11/1997 | Wideman |

(Continued)

FOREIGN PATENT DOCUMENTS
AU    1997/10082    1/1997
(Continued)

OTHER PUBLICATIONS
002479646 XP, Dec. 3, 1996, Takahashi.
(Continued)

*Primary Examiner* — Mark Eashoo
*Assistant Examiner* — Angela C Scott
(74) *Attorney, Agent, or Firm* — Dominick G. Vicari; Joseph S. Ostroff (57) ABSTRACT This invention relates to novel sulfur-containing silane coupling agents, and organic polymers containing carbon-carbon double bonds. These novel silanes can be carried on organic and inorganic fillers. The invention also relates to articles of manufacture, particularly tires, made from the elastomer compositions described herein.

63 Claims, 1 Drawing Sheet

U.S. PATENT DOCUMENTS

| | | | |
|---|---|---|---|
| 5,698,619 | A | 12/1997 | Cohen et al. |
| 5,719,207 | A | 2/1998 | Cohen et al. |
| 5,723,529 | A | 3/1998 | Bernard et al. |
| 5,728,778 | A | 3/1998 | D'Sidocky et al. |
| 5,733,963 | A | 3/1998 | Sandstrom et al. |
| 5,753,732 | A | 5/1998 | Wideman et al. |
| 5,770,754 | A | 6/1998 | Scholl |
| 5,780,531 | A | 7/1998 | Scholl |
| 5,817,852 | A | 10/1998 | Ichinohe et al. |
| 5,827,912 | A | 10/1998 | Scholl |
| 5,859,275 | A | 1/1999 | Munzenberg et al. |
| 5,977,225 | A | 11/1999 | Scholl |
| 6,046,349 | A | 4/2000 | Batz-Sohn et al. |
| 6,127,468 | A | 10/2000 | Cruse et al. |
| 6,140,393 | A | 10/2000 | Bomai et al. |
| 6,140,524 | A | 10/2000 | Ichonoke et al. |
| 6,194,594 | B1 | 2/2001 | Gori et al. |
| 6,194,595 | B1 | 2/2001 | Michel et al. |
| 6,204,339 | B1 | 3/2001 | Waldman et al. |
| 6,211,345 | B1 | 4/2001 | Weller |
| 6,268,421 | B1 | 7/2001 | Dittrich et al. |
| 6,359,046 | B1 | 3/2002 | Cruse |
| 6,407,153 | B1 | 6/2002 | Von Hellens |
| 6,414,061 | B1 | 7/2002 | Cruse et al. |
| 6,420,488 | B1 | 7/2002 | Penot |
| 6,518,367 | B1 | 2/2003 | Yatsuyanagi et al. |
| 6,528,673 | B2 | 3/2003 | Cruse et al. |
| 6,608,125 | B2 | 8/2003 | Cruse et al. |
| 6,649,684 | B1 | 11/2003 | Okel |
| 6,683,135 | B2 | 1/2004 | Cruse et al. |
| 6,759,545 | B2 | 7/2004 | Yanagisawa et al. |
| 6,777,569 | B1 | 8/2004 | Westmeyer et al. |
| 6,849,754 | B2 | 2/2005 | Deschler et al. |
| 6,890,981 | B1 | 5/2005 | Luginsland |
| 6,984,689 | B2 | 1/2006 | Penot et al. |
| 6,984,711 | B2 | 1/2006 | Wonmun et al. |
| 7,041,843 | B2 | 5/2006 | Yanagisawa et al. |
| 7,122,590 | B2 | 10/2006 | Cruse et al. |
| 7,138,537 | B2 | 11/2006 | Cruse et al. |
| 7,166,735 | B2 | 1/2007 | Yanagisawa et al. |
| 7,186,768 | B2 | 3/2007 | Korth et al. |
| 7,199,256 | B2 | 4/2007 | Yanagisawa et al. |
| 7,217,751 | B2 | 5/2007 | Durel et al. |
| 7,288,667 | B2 | 10/2007 | Yanagisawa |
| 7,301,042 | B2 | 11/2007 | Cruse |
| 7,307,121 | B2 | 12/2007 | Zhang et al. |
| 7,309,797 | B2 | 12/2007 | Yanagisawa |
| 7,355,059 | B2 | 4/2008 | Yanagisawa |
| 7,368,588 | B2 | 5/2008 | Yanagisawa |
| 2002/0002220 | A1 | 1/2002 | Reedy et al. |
| 2002/0055564 | A1 | 5/2002 | Cruse et al. |
| 2003/0130388 | A1 | 7/2003 | Luginsland et al. |
| 2003/0199619 | A1 | 10/2003 | Cruse |
| 2003/0200900 | A1 | 10/2003 | Korth et al. |
| 2003/0225195 | A1 | 12/2003 | Cruse et al. |
| 2004/0143037 | A1 | 7/2004 | Chang et al. |
| 2004/0147651 | A1 | 7/2004 | Barruel et al. |
| 2004/0210001 | A1 | 10/2004 | Cruse et al. |
| 2004/0220307 | A1 | 11/2004 | Wu |
| 2005/0009955 | A1 | 1/2005 | Cohen |
| 2005/0027060 | A1 | 2/2005 | Yagi et al. |
| 2005/0176861 | A1 | 8/2005 | Nakayama et al. |
| 2005/0245753 | A1 | 11/2005 | Cruse et al. |
| 2005/0245754 | A1 | 11/2005 | Glatzer et al. |
| 2006/0036034 | A1 | 2/2006 | Chaves et al. |
| 2006/0106143 | A1 | 5/2006 | Lin et al. |
| 2006/0177657 | A1 | 8/2006 | Weller |
| 2006/0205907 | A1 | 9/2006 | Guyer |
| 2006/0235236 | A1 | 10/2006 | Simandan |
| 2006/0281841 | A1 | 12/2006 | Weller et al. |
| 2007/0037915 | A1 | 2/2007 | Masumoto |
| 2007/0135572 | A1 | 6/2007 | Wolter |
| 2007/0197812 | A1 | 8/2007 | Chaves et al. |
| 2007/0197813 | A1 | 8/2007 | Chaves et al. |
| 2008/0027162 | A1 | 1/2008 | Hua et al. |
| 2008/0161452 | A1 | 7/2008 | York et al. |
| 2008/0161460 | A1 | 7/2008 | York et al. |
| 2008/0161461 | A1 | 7/2008 | Cruse et al. |
| 2008/0161462 | A1 | 7/2008 | York et al. |
| 2008/0161463 | A1 | 7/2008 | Cruse et al. |
| 2008/0161475 | A1 | 7/2008 | York et al. |
| 2008/0161477 | A1 | 7/2008 | Cruse et al. |
| 2008/0161486 | A1 | 7/2008 | York et al. |
| 2008/0161590 | A1 | 7/2008 | Cruse et al. |

FOREIGN PATENT DOCUMENTS

| | | |
|---|---|---|
| CA | 991836 | 6/1976 |
| CA | 1018991 | 10/1977 |
| CA | 2103653 | 2/1994 |
| CA | 2186060 | 3/1997 |
| CA | 2231302 | 9/1998 |
| CA | 2146333 | 5/2010 |
| DE | 2141159 | 3/1973 |
| DE | 2141160 | 3/1973 |
| DE | 2255577 | 6/1974 |
| DE | 2360471 | 6/1975 |
| DE | 2405758 | 8/1975 |
| DE | 2536674 | 2/1977 |
| DE | 2747277 | 4/1979 |
| DE | 2819638 | 11/1979 |
| DE | 2848559 | 5/1980 |
| DE | 2856229 | 7/1980 |
| DE | 3028365 | 2/1982 |
| DE | 3305373 | 8/1984 |
| DE | 3314742 | 10/1984 |
| DE | 3311340 | 11/1984 |
| DE | 3437473 | 4/1986 |
| DE | 4023537 | 1/1992 |
| DE | 4119959 | 12/1992 |
| DE | 4128203 | 5/1993 |
| DE | 4236218 | 6/1993 |
| DE | 4225978 | 4/1994 |
| DE | 43088311 | 9/1994 |
| DE | 19702046 | 1/1998 |
| DE | 19819373 | 11/1999 |
| DE | 10222509 | 3/2003 |
| DE | 4004781 | 5/2010 |
| EP | 0784072 | 7/1977 |
| EP | 0845493 | 6/1996 |
| EP | 0764687 | 3/1997 |
| EP | 0784072 | 7/1997 |
| EP | 0795577 | 9/1997 |
| EP | 0680997 | 9/1998 |
| EP | 0864605 | 9/1998 |
| EP | 0732362 | 6/1999 |
| EP | 0773224 | 12/2001 |
| EP | 0631982 | 1/2002 |
| EP | 0955302 | 6/2002 |
| EP | 0919559 | 11/2002 |
| EP | 0848006 | 8/2003 |
| EP | 1394167 | * 3/2004 |
| EP | 1491545 | 12/2004 |
| EP | 0738748 | 8/2005 |
| EP | 1270657 | 3/2006 |
| EP | 1634726 | 3/2006 |
| EP | 1514892 | 7/2006 |
| EP | 1714984 | 10/2006 |
| FR | 2804104 | 7/2001 |
| GB | 1439247 | 6/1976 |
| GB | 2259303 | 10/1993 |
| JP | 63-270751 | 8/1988 |
| JP | 8319225 | 12/1996 |
| JP | 2000-154380 | 6/2000 |
| JP | 2001-226383 | 8/2001 |
| JP | 2001-226532 | 8/2001 |
| JP | 2005-263127 | 9/2005 |
| JP | 2005-263998 | 9/2005 |
| JP | 2005-263999 | 9/2005 |
| JP | 2005-272630 | 10/2005 |
| JP | 2005-281621 | 10/2005 |
| JP | 2005-320317 | 11/2005 |
| JP | 2005-320374 | 11/2005 |
| JP | 2006-28245 | 2/2006 |
| JP | 2006-28253 | 2/2006 |
| JP | 2006-28430 | 2/2006 |
| JP | 2006-104455 | 4/2006 |
| JP | 2006-213777 | 8/2006 |
| JP | 2006-213803 | 8/2006 |
| JP | 2006-225448 | 8/2006 |

| | | |
|---|---|---|
| JP | 2006-232881 | 9/2006 |
| JP | 2006-232916 | 9/2006 |
| JP | 2006-232917 | 9/2006 |
| JP | 2007-51169 | 3/2007 |
| KR | 10-2005-0025817 | 3/2005 |
| WO | 98/53004 | 11/1998 |
| WO | 99/07713 | 2/1999 |
| WO | 99/09036 | 2/1999 |
| WO | 00/05300 | 2/2000 |
| WO | 00/53671 | 9/2000 |
| WO | 01/46202 | 6/2001 |
| WO | 02/20534 | 3/2002 |
| WO | 02/48256 | 6/2002 |
| WO | 03/035252 | 5/2003 |
| WO | 04000930 | 12/2003 |
| WO | 2004/005395 | 1/2004 |
| WO | 2005/007660 | 1/2005 |
| WO | 2005/007661 | 1/2005 |
| WO | 2006/113122 | 10/2006 |
| WO | 2007/039416 | 4/2007 |
| WO | 2007/068555 | 6/2007 |
| WO | 2007/085521 | 8/2007 |
| WO | 2007/132909 | 11/2007 |
| WO | 2008/074567 | 6/2008 |

OTHER PUBLICATIONS

002479812 XP, Nov. 20, 2007, Chem. Abstract.
Abstract for Japanese Pat. Appl. Publ. No. 2001-226383. A published Aug. 21, 2001 (Patent Abstracts for Japan, 1 page) (corresp. To FP2 on attached PTO/SB/08a form).
Abstract for Japanese Pat. Appl. Publ. No. 2001-226532A published Aug. 21, 2001 (Patent Abstracts for Japan, 1 page) (corresp. To FP3 on attached PTO/SB/08a form).
Harris, et al., "Ruthenium-catalysed ortho alkylation of hydroxyacetophenones; the functionalisation of ring C aromatic diterpenoids;" Journal of Organometallic Chemistry, 530 (1997) 211-223.

* cited by examiner

Figure 1

SILATED CYCLIC CORE POLYSULFIDES, THEIR PREPARATION AND USE IN FILLED ELASTOMER COMPOSITIONS

CROSS-REFERENCE TO RELATED APPLICATIONS

The present application is a continuation of U.S. application Ser. No. 11/647,901 filed Dec. 28, 2006 now U.S. Pat. No. 7,687,558 to which priority is claimed and which is herein incorporated by reference in its entirety.

The present application is related to the following applications, filed on even date herewith, with the disclosures of each the applications being incorporated by reference herein in their entireties:

application Ser. No. 11/617,683, filed on Dec. 28, 2006, entitled "Tire Compositions And Components Containing Silated Cyclic Core Polysulfides".

U.S. application Ser. No. 11/617,649, filed on Dec. 28, 2006, entitled "Tire Compositions And Components Containing Free-Flowing Filler Compositions".

U.S. application Ser. No. 11/617,678, filed on Dec. 28, 2006, entitled "Tire Compositions And Components Containing Free-Flowing Filler Compositions".

U.S. application Ser. No. 11/617,663, filed on Dec. 28, 2006, entitled "Tire Compositions And Components Containing Silated Core Polysulfides".

U.S. application Ser. No. 11/617,659, filed on Dec. 28, 2006, entitled "Tire Compositions And Components Containing Blocked Mercaptosilane Coupling Agent".

U.S. application Ser. No. 11/648,460, filed on Dec. 28, 2006, entitled "Free-Flowing Filler Composition And Rubber Composition Containing Same".

U.S. application Ser. No. 11/647,903, filed on Dec. 28, 2006, entitled "Free-Flowing Filler Composition And Rubber Composition Containing Same".

U.S. application Ser. No. 11/647,780, filed on Dec. 28, 2006, entitled "Blocked Mercaptosilane Coupling Agents, Process For Making And Uses In Rubber".

U.S. application Ser. No. 11/648,287, filed on Dec. 28, 2006, entitled "Silated Core Polysulfides, Their Preparation And Use In Filled Elastomer Compositions".

The present application is directed to an invention which was developed pursuant to a joint research agreement wherein the meaning of 35 U.S.C. §103(c). The joint research agreement dated May 7, 2001 as amended, between Continental AG, and General Electric Company, on behalf of GE Advanced Materials, Silicones Division, now Momentive Performance Materials Inc.

FIELD OF THE INVENTION

The present invention generally relates to silated cyclic core polysulfides compositions, process for their preparation, and rubber compositions comprising same.

BACKGROUND OF THE INVENTION

Sulfur-containing coupling agents used for mineral-filled elastomers involve silanes in which two alkoxysilylalkyl groups are bound, each to one end of a chain of sulfur atoms. The two alkoxysilyl groups are bonded to the chain of sulfur atoms by two similar, and in most cases, identical, hydrocarbon fragments. The general silane structures just described, hereinafter referred to as "simple bis polysulfide silanes," usually contain a chain of three methylene groups as the two mediating hydrocarbon units. In some cases, the methylene chain is shorter, containing only one or two methylenes per chain. The use of these compounds is primarily as coupling agents for mineral-filled elastomers. These coupling agents function by chemically bonding silica or other mineral fillers to polymer when used in rubber applications. Coupling is accomplished by chemical bond formation between the silane sulfur and the polymer and by hydrolysis of the alkoxysilyl groups and subsequent condensation with silica hydroxyl groups. The reaction of the silane sulfur with the polymer occurs when the S—S bonds are broken and the resulting fragment adds to the polymer. A single linkage to the polymer occurs for each silyl group bonded to the silica. This linkage contains a single, relatively weak C—S and/or S—S bond(s) that forms the weak link between the polymer and the silica. Under high stress, this single C—S and/or S—S linkages may break and therefore contribute to wear of the filled elastomer.

The use of polysulfide silanes coupling agents in the preparation of rubber is well known. These silanes contain two silicon atoms, each of which is bound to a disubstituted hydrocarbon group, and three other groups of which at least one is removable from silicon by hydrolysis. Two such hydrocarbon groups, each with their bound silyl group, are further bound to each end of a chain of at least two sulfur atoms. These structures thus contain two silicon atoms and a single, continuous chain of sulfur atoms of variable length.

Hydrocarbon core polysulfide silanes that feature a central molecular core isolated from the silicon in the molecule by sulfur-sulfur bonds are known in the art. Polysufide silanes containing a core that is an aminoalkyl group separated from the silicon atom by a single sulfur and a polysulfide group and where the polysulfide group is bonded to the core at a secondary carbon atom are also know in the art. As well as core fragments in which only two polysulfide groups are attached to the core.

When the polysulfide groups are attached directly to an aromatic core, the reactivity with the polymer (rubber) is reduced. The aromatic core is sterically bulky which inhibits the reaction. Compositions in which the polysulfides are attached directly to cyclic aliphatic fragments derived by vinyl cyclohexene contain more than one silated core and form large rings. The cyclohexyl core is sterically more hindered than the aromatic core and is less reactive. Although these compositions can form more than one sulfur linkage to the polymer rubber for each attachment of the coupling agent to the silica through the silyl group, their effectiveness is low due to the low reactivity.

The low reactivity is due to the attachment of the polysulfide to the secondary carbon of cyclic core structure. The positioning of the polysulfide group is not optimal for reaction with the accelerators and reaction with the polymer.

The present invention overcomes the deficiencies of the aforementioned compositions involving silane coupling agents in several ways. The silanes of the present invention described herein are not limited to two silyl groups nor to one chain of sulfur atoms. In fact the molecular architecture in which multiple polysulfide chains are oriented in a noncollinear configuration (i.e. branched, in the sense that the branch points occur within the carbon backbone interconnecting the polysulfide chains) is novel.

The silanes of the present invention have advantages over that in the prior art by providing a means to multiple points of sulfur attachment to polymer per point of silicon attachment to filler. The silanes described herein may be asymmetric with regard to the groups on the two ends of the sulfur chains. The silyl groups, rather than occurring at the ends of the molecule, tend to occur more centrally and are chemically bonded to the cyclic core through carbon-carbon, carbon-sulfur and car- bon-silicon bonds. The carbon-sulfur bonds of the thio ester linkages (sulfide) are more stable than the sulfur-sulfur bonds of the disulfide or polysulfide functional groups. These thio ether groups are therefore less likely to react with the accelerators and curing agents or to decompose when subjected to high shear or temperatures normally associated with the mixing and curing of rubber compounds. The thio ether linkage also provides a convenient synthetic route for making the silanes of the present invention. The cyclic core also contains multiple polysulfide groups that are attached to ring by means of a divalent, straight chain alkylene group. The attachment of the polysulfide group to the primary carbon of the alkylene group decreases significantly the steric hinderance of the core, and increases the reactivity of the polysulfides with the polymer. In addition, the cyclic core orients these alkylene chains containing the polysulfide groups away from each other to further reduce the steric hindrance near the polysulfide groups. This distinction is what allows silica to become and remain bonded (through the intermediacy of a sequence of covalent chemical bonds) to polymer at multiple points using the silanes of the present invention.

The examples presented herein demonstrate that the silanes of the present invention impart a desirable balance of physical properties (performance to mineral-filled elastomer compositions) and better wear characteristics to articles manufactured from these elastomers. Improvements in rolling resistance are also apparent for elastomers used in tire applications.

SUMMARY OF THE INVENTION

In a first embodiment of the present invention, novel silated cyclic core polysulfides of the present invention can be represented by Formula (1)

$$[Y^1R^1S_x-]_m[G^1(SR^2SiX^1X^2X^3)_a]_n[G^2]_o[R^3Y^2]_p \quad \text{(Formula 1)}$$

wherein each occurrence of $G^1$ is independently selected from polyvalent cyclic hydrocarbon or heterocarbon species having from 1 to about 30 carbon atoms and containing a polysulfide group represented by Formula (2)

$$[(CH_2)_b-]_cR^4[-(CH_2)_dS_x-]_e; \quad \text{(Formula 2)}$$

each occurrence of $G^2$ is independently selected from a polyvalent cyclic hydrocarbon or heterocarbon species of 1 to about 30 carbon atoms and containing a polysulfide group represented by Formula (3)

$$[(CH_2)_b-]_cR^5[-(CH_2)_dS_x-]_e; \quad \text{(Formula 3)}$$

each occurrence of $R^1$ and $R^3$ are independently selected from a divalent hydrocarbon fragment having from 1 to about 20 carbon atoms that include branched and straight chain alkyl, alkenyl, alkynyl, aryl or aralkyl groups in which one hydrogen atom was substituted with a $Y^1$ or $Y^2$ group;

each occurrence of $Y^1$ and $Y^2$ is independently selected from, but not limited to silyl (—$SiX^1X^2X^3$), alkoxy (—$OR^6$), hydrogen, carboxylic acid (—C(=O)OH), ester (—C(=O)$OR^6$, in which $R^6$ is any monovalent hydrocarbon group having from 1 to 20 carbon atoms, and includes branched or straight chain alkyl, alkenyl, aryl or aralkyl groups, and the like;

each occurrence of $R^2$ is independently selected from a divalent hydrocarbon fragment having from 1 to about 20 carbon atoms that include branched and straight chain alkyl, alkenyl, alkynyl, aryl or aralkyl groups;

each occurrence of $R^4$ is independently selected from a polyvalent cyclic hydrocarbon fragment of 1 to about 28 carbon atom that was obtained by substitution of hydrogen atoms equal to the sum of a+c+e, and include cyclic and polycyclic alkyl, alkenyl, alkynyl, aryl and aralkyl groups in which a+c+e−1 hydrogens have been replaced, or a polyvalent cyclic heterocarbon fragment from 1 to 27 carbon atoms that was obtained by substitution of hydrogen atoms equal to the sum of a+c+e;

each occurrence of $R^5$ is independently selected from a polyvalent cyclic hydrocarbon fragment of 1 to about 28 carbon atom that was obtained by substitution of hydrogen atoms equal to the sum of c+e, and include cyclic and polycyclic alkyl, alkenyl, alkynyl, aryl and aralkyl groups in which c+e−1 hydrogens have been replaced, or a polyvalent cyclic heterocarbon fragment from 1 to 27 carbon atoms that was obtained by substitution of hydrogen atoms equal to the sum of c+e;

each occurrence of $X^1$ is independently selected from hydrolyzable groups consisting of —Cl, —Br, —OH, —$OR^6$, and $R^6C$(=O)O—, wherein $R^6$ is any monovalent hydrocarbon group having from 1 to 20 carbon atoms, and includes branched or straight chain alkyl, alkenyl, aryl or aralkyl groups;

each occurrence of $X^2$ and $X^3$ is independently selected from the group consisting of hydrogen, the members listed above for $R^6$, the members listed above for $X^1$ and —OSi containing groups that result from the condensation of silanols;

each occurrence of the subscripts, a, b, c, d, e, m, n, o, p, and x, is independently given by a is 1 to about 3; b is 1 to about 5; c is 1 to about 3; d is 1 to about 5; e is 1 to about 3; m is 1 to about 100, n is 1 to about 15; o is 0 to about 10; p is 1 to about 100, and x is 1 to about 10.

In a second embodiment of the present invention, a process for the preparation of the silated cyclic core polysulfide composition comprising reacting a cyclic hydrocarbon or cyclic heterocarbon containing vinyl groups with a thioacid, the acyl group is removed, and the mercapto groups are reacted with base and a halo containing hydrocarbon silane and finally base, sulfur and a halo containing substituted hydrocarbon.

In accordance with a third embodiment of the present invention, a rubber composition is provided comprising (a) a silated cyclic core polysulfide composition having the general formula:

$$[Y^1R^1S_x-]_m[G^1(SR^2SiX^1X^2X^3)_a]_n[G^2]_o[R^3Y^2]_p$$

wherein $Y^1$, $R_1$, $G^1$, $R^2$, $X^1$, $X^2$, $X^3$, $G^2$, $R^3$, $Y^2$, a, o, p, x, m, and n have the aforestated meanings; (b) an inorganic filler; and (c) a rubber.

DETAILED DESCRIPTION OF THE PRESENT INVENTION

The novel silated cyclic core polysulfides of the present invention are represented by Formula (1)

$$[Y^1R^1S_x-]_m[G^1(SR^2SiX^1X^2X^3)_a]_n[G^2]_o[R^3Y^2]_p \quad \text{(Formula 1)}$$

wherein each occurrence of $G^1$ is independently selected from polyvalent cyclic hydrocarbon or heterocarbon species having from 1 to about 30 carbon atoms and containing a polysulfide group represented by Formula (2)

$$[(CH_2)_b-]_cR^4[-(CH_2)_dS_x-]_e; \quad \text{(Formula 2)}$$

each occurrence of $G^2$ is independently selected from polyvalent cyclic hydrocarbon or heterocarbon species of 1 to about 30 carbon atoms and containing a polysulfide group represented by Formula (3)

$$[(CH_2)_b—]_c R^5 [—(CH_2)_d S_x—]_e;\qquad\text{(Formula 3)}$$

each occurrence of $R^1$ and $R^3$ are independently selected from a divalent hydrocarbon fragment having from 1 to about 20 carbon atoms that include branched and straight chain alkyl, alkenyl, alkynyl, aryl or aralkyl groups in which one hydrogen atom was substituted with a $Y^1$ or $Y^2$ group; each occurrence of $Y^1$ and $Y^2$ is independently selected from, but not limited to silyl ($—SiX^1X^2X^3$), alkoxy ($—OR^6$), hydrogen, carboxylic acid ($—C(=O)OH$), ester ($—C(=O)OR^6$, wherein $R^6$ is a monovalent hydrocarbon group having from 1 to 20 carbon atoms, and includes branched or straight chain alkyl, alkenyl, aryl or aralkyl groups, and the like;

each occurrence of $R^2$ is independently selected from a divalent hydrocarbon fragment having from 1 to about 20 carbon atoms that include branched and straight chain alkyl, alkenyl, alkynyl, aryl or aralkyl groups;

each occurrence of $R^4$ is independently selected from a polyvalent cyclic hydrocarbon fragment of 1 to about 28 carbon atom that was obtained by substitution of hydrogen atoms equal to the sum of a+c+e, and include cyclic and polycyclic alkyl, alkenyl, alkynyl, aryl and aralkyl groups in which a+c+e−1 hydrogens have been replaced, or a polyvalent cyclic heterocarbon fragment from 1 to 27 carbon atoms that was obtained by substitution of hydrogen atoms equal to the sum of a+c+e;

each occurrence of $R^5$ is independently selected from a polyvalent cyclic hydrocarbon fragment of 1 to about 28 carbon atom that was obtained by substitution of hydrogen atoms equal to the sum of c+e and include cyclic and polycyclic alkyl, alkenyl, alkynyl, aryl and aralkyl groups in which c+e−1 hydrogens have been replaced, or a polyvalent cyclic heterocarbon fragment from 1 to 27 carbon atoms that was obtained by substitution of hydrogen atoms equal to the sum of c+e;

each occurrence of $X^1$ is independently selected from hydrolyzable groups consisting of —Cl, —Br, —OH, —OR$^6$, and $R^6C(=O)O—$, wherein $R^6$ is any monovalent hydrocarbon group having from 1 to 20 carbon atoms, and includes branched or straight chain alkyl, alkenyl, aryl or aralkyl groups;

each occurrence of $X^2$ and $X^3$ is independently selected from the group consisting of hydrogen, the members listed above for $R^6$, the members listed above for $X^1$ and —OSi containing groups that result from the condensation of silanols; each occurrence of the subscripts, a, b, c, d, e, m, n, o, p, and x, is independently given by a is 1 to about 3; b is 1 to about 5; c is 1 to about 3; d is 1 to about 5; e is 1 to about 3; m is 1 to about 100, n is 1 to about 15; o is 0 to about 10; p is 1 to about 100, and x is 1 to about 10.

The term, "heterocarbon", as used herein, refers to any hydrocarbon structure in which the carbon-carbon bonding backbone is interrupted by bonding to atoms of nitrogen and/or oxygen, or in which the carbon-carbon bonding backbone is interrupted by bonding to groups of atoms containing sulfur, nitrogen and/or oxygen, such as cyanurate ($C_3N_3$). Heterocarbon fragments also refer to any hydrocarbon in which a hydrogen or two or more hydrogens bonded to carbon are replaced with a sulfur, oxygen or nitrogen atom, such as a primary amine ($—NH_2$), and oxo ($=O$), and the like.

Thus, $R^4$ and $R^5$ include, but is not limited to cyclic, and/or polycyclic polyvalent aliphatic hydrocarbons that may be substituted with alkyl, alkenyl, alkynyl, aryl and/or aralkyl groups; cyclic and/or polycyclic polyvalent heterocarbon optionally containing ether functionality via oxygen atoms each of which is bound to two separate carbon atoms, polysulfide functionality, in which the polysulfide group ($—S_x—$) is bonded to two separate carbon atoms on $G^1$ or $G^2$ to form a ring, tertiary amine functionality via nitrogen atoms each of which is bound to three separate carbon atoms, cyano (CN) groups, and/or cyanurate ($C_3N_3$) groups; aromatic hydrocarbons; and arenes derived by substitution of the aforementioned aromatics with branched or straight chain alkyl, alkenyl, alkynyl, aryl and/or aralkyl groups.

As used herein, "alkyl" includes straight, branched and cyclic alkyl groups; "alkenyl" includes any straight, branched, or cyclic alkenyl group containing one or more carbon-carbon double bonds, where the point of substitution can be either at a carbon-carbon double bond or elsewhere in the group; and "alkynyl" includes any straight, branched, or cyclic alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Examples of alkyls include, but are not limited to, methyl, ethyl, propyl, isobutyl. Examples of alkenyls include vinyl, but are not limited to, propenyl, allyl, methallyl, ethylidenyl norbornane, ethylidene norbornyl, ethylidenyl norbornene, and ethylidene norbornenyl. Some examples of alkynyls include, but are not limited to, acetylenyl, propargyl, and methylacetylenyl.

As used herein, "aryl" includes any aromatic hydrocarbon from which one hydrogen atom has been removed; "aralkyl" includes any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents. Some examples of aryls include, but are not limited to, phenyl and naphthalenyl. Examples of aralkyls include, but are not limited to, benzyl and phenethyl, and some examples of arenyls include tolyl and xylyl.

As used herein, "cyclic alkyl", "cyclic alkenyl", and "cyclic alkynyl" also include bicyclic, tricyclic, and higher cyclic structures, as well as the aforementioned cyclic structures further substituted with alkyl, alkenyl, and/or alkynyl groups. Representative examples include, but are not limited to, norbornyl, norbornenyl, ethylnorbornyl, ethylnorbornenyl, cyclohexyl, ethylcyclohexyl, ethylcyclohexenyl, cyclohexylcyclohexyl, and cyclododecatrienyl, and the like.

Representative examples of $X^1$ include, but are not limited to, methoxy, ethoxy, propoxy, isopropoxy, butoxy, phenoxy, benzyloxy, hydroxy, chloro, and acetoxy. Representative examples of $X^2$ and $X^3$ include the representative examples listed above for $X^1$ as well as hydrogen, methyl, ethyl, propyl, isopropyl, sec-butyl, phenyl, vinyl, cyclohexyl, and higher straight-chain alkyl, such as butyl, hexyl, octyl, lauryl, and octadecyl, and the like.

Representative examples of $R^1$, $R^2$ and $R^3$ include the terminal straight-chain alkyls further substituted terminally at the other end, such as $—CH_2—$, $—CH_2CH_2—$, $—CH_2CH_2CH_2—$, and $—CH_2CH_2CH_2CH_2CH_2CH_2CH_2—$, and their beta-substituted analogs, such as $—CH_2(CH_2)_u CH(CH_3)—$, where u is zero to 17; the structure derivable from methallyl chloride, $—CH_2CH(CH_3)CH_2—$; any of the structures derivable from divinylbenzene, such as $—CH_2CH_2(C_6H_4)CH_2CH_2—$ and $—CH_2CH_2(C_6H_4)CH(CH_3)—$, where the notation $C_6H_4$ denotes a disubstituted benzene ring; any of the structures derivable from diallylether, such as —CH₂CH₂CH₂OCH₂CH₂CH₂— and —CH₂CH₂CH₂OCH₂CH(CH₃)—; any of the structures derivable from butadiene, such as —CH₂CH₂CH₂CH₂—, —CH₂CH₂CH(CH₃)—, and —CH₂CH(CH₂CH₃)—; any of the structures derivable from piperylene, such as —CH₂CH₂CH₂CH(CH₃)—, —CH₂CH₂CH(CH₂CH₃)—, and —CH₂CH(CH₂CH₂CH₃)—; any of the structures derivable from isoprene, such as —CH₂CH(CH₃)CH₂CH₂—, —CH₂CH(CH₃)CH(CH₃)—, —CH₂C(CH₃)(CH₂CH₃)—, —CH₂CH₂CH(CH₃)CH₂—, —CH₂CH₂C(CH₃)₂— and —CH₂CH[CH(CH₃)₂]—; any of the isomers of —CH₂CH₂-norbornyl-, —CH₂CH₂-cyclohexyl-; any of the diradicals obtainable from norbornane, cyclohexane, cyclopentane, tetrahydrodicyclopentadiene, or cyclododecene by loss of two hydrogen atoms; the structures derivable from limonene, —CH₂CH(4-methyl-1-C₆H₉—)CH₃, where the notation C₆H₉ denotes isomers of the trisubstituted cyclohexane ring lacking substitution in the 2 position; any of the monovinyl-containing structures derivable from trivinylcyclohexane, such as —CH₂CH₂(vinylC₆H₉)CH₂CH₂— and —CH₂CH₂(vinylC₆H₉)CH(CH₃)—, where the notation C₆H₉ denotes any isomer of the trisubstituted cyclohexane ring; any of the monounsaturated structures derivable from myrcene containing a trisubstituted C=C, such as —CH₂CH[CH₂CH₂CH=C(CH₃)₂]CH₂CH₂—, —CH₂CH[CH₂CH₂CH=C(CH₃)₂]CH(CH₃)—, —CH₂C[CH₂CH₂CH=C(CH₃)₂](CH₂CH₃)—, —CH₂CH₂CH[CH₂CH₂CH=C(CH₃)₂]CH₂—, —CH₂CH₂(C—)(CH₃)[CH₂CH₂CH=C(CH₃)₂], and —CH₂CH[CH(CH₃)[CH₂CH₂CH=C(CH₃)₂]]—; and any of the monounsaturated structures derivable from myrcene lacking a trisubstituted C=C, such as —CH₂CH(CH=CH₂)CH₂CH₂CH₂C(CH₃)₂—, —CH₂CH(CH=CH₂)CH₂CH₂CH[CH(CH₃)₂]—, —CH₂C(=CH—CH₃)CH₂CH₂CH₂C(CH₃)₂—, —CH₂C(=CH—CH₃)CH₂CH₂CH[CH(CH₃)₂]—, —CH₂CH₂C(=CH₂)CH₂CH₂CH₂C(CH₃)₂—, —CH₂CH₂C(=CH₂)CH₂CH₂CH[CH(CH₃)₂]—, —CH₂CH=C(CH₃)₂CH₂CH₂CH₂C(CH₃)₂—, and —CH₂CH=C(CH₃)₂CH₂CH₂CH[CH(CH₃)₂].

Representative examples of G¹ include, but are not limited to, structures derivable from divinylbenzene, such as —CH₂CH₂(C₆H₄)CH(CH₂—)— and —CH₂CH₂(C₆H₃—)CH₂CH₂—, —CH₂(CH—)(C₆H₄)CH(CH₂—)—, where the notation C₆H₄ denotes a disubstituted benzene ring and C₆H₃— denotes a trisubstituted ring; any structures derivable from trivinylcyclohexane, such as —CH₂(CH—)(vinylC₆H₉)CH₂CH₂—; (—CH₂CH₂)₃C₆H₉, and (—CH₂CH₂)₂C₆H₉CH(CH₃)—, —CH₂(CH—)(vinylC₆H₉)(CH—)CH₂—, —CH₂CH₂C₆H₉—[(CH—) CH₂—]₂, —CH(CH₃)C₆H₉—[(CH—)CH₂—]₂, and C₆H₉—[(CH—)CH₂—]₃, —CH₂(CH—)C₆H₉—[CH₂CH₂—]₂, and —CH₂(CH—)C₆H₉—[CH(CH₃)—][CH₂CH₂—], where the notation C₆H₉ denotes any isomer of the trisubstituted cyclohexane ring.

Representative examples of G² include, but are not limited to, structures derivable from divinylbenzene, such as —CH₂CH₂(C₆H₄)CH₂CH₂—, —CH₂CH₂(C₆H₄)CH(CH₂—)— and —CH₂CH₂(C₆H₃—)CH₂CH₂—, —CH₂(CH—)(C₆H₄)CH(CH₂—)—, where the notation C₆H₄ denotes a disubstituted benzene ring; any structures derivable from trivinylcyclohexane, such as —CH₂CH₂(vinylC₆H₉)CH₂CH₂—, and (—CH₂CH₂)C₆H₉CH₂CH₃, —CH₂(CH—)(vinylC₆H₉)CH₂CH₂—, (—CH₂CH₂)₃C₆H₉, and (—CH₂CH₂)₂C₆H₉CH(CH₃)—, —CH₂(CH—)(vinylC₆H₉)(CH—)CH₂—, —CH₂CH₂C₆H₉—[(CH—)CH₂—]₂, —CH(CH₃)C₆H₉[CH—)CH₂—]₂, and C₆H₉—[(CH—)CH₂—]₃, —CH₂(CH—)C₆H₉—[CH₂CH₂—]₂, and —CH₂(CH—)C₆H₉—[CH(CH₃)—][CH₂CH₂—], where the notation C₆H₉ denotes any isomer of the trisubstituted cyclohexane ring.

Representative examples of silated cyclic core polysulfide silanes of the present invention include any of the isomers of 4-(6-triethoxysilyl-3-thiahexyl)-1,2-bis-(13-triethoxysilyl-3,4,5,6-tetrathiamidecyl)cyclohexane; 4-(6-triethoxysilyl-3-thiahexyl)-1,2-bis-(13-triethoxysilyl-3,4-dithiamidecyl)cyclohexane; 4-(6-triethoxysilyl-3-thiahexyl)-1,2-bis-(13-triethoxysilyl-3,4,5-trithiamidecyl)cyclohexane; 4-(6-triethoxysilyl-3-thiahexyl)-1,2-bis-(12-triethoxysilyl-3,4,5-tetrathiadodecyl)cyclohexane; 1-(6-triethoxysilyl-3-thiahexyl)-2,4-bis-(11-triethoxysilyl-3,4-tetrathiaunidecyl)cyclohexane 4-(3-triethoxysilyl-1-thiaethyl)-1,2-bis-(13-triethoxysilyl-3,4,5,6,7-pentathiamidecyl)cyclohexane; 4-(6-diethoxymethylsilyl-2-thia hexyl)-1,2-bis-(13-triethoxysilyl-3,4,5,6-tetrathiamidecyl)cyclohexane; 4-(4-triethoxysilyl-2-thiabutyl)-1,2-bis-(9-triethoxysilyl-3,4,5,6-tetrathianonyl)cyclohexane; 4-(7-triethoxysilyl-3-thiaheptyl)-1,2-bis-(9-triethoxysilyl-3,4,5-trithianonyl)cyclohexane; 4-(5-triethoxysilyl-2-thiapentyl)-1,2-bis-(9-triethoxysilyl-3,4,5,6-tetrathianonyl)benzene; 4-(5-triethoxysilyl-2-thiapentyl)-1,2-bis-(9-triethoxysilyl-3,4,5-trithianonyl)benzene; 4-(5-triethoxysilyl-2-thiapentyl)-1,2-bis-(9-triethoxysilyl-3,4-dithianonyl)benzene; bis-2-[4-(3-triethoxysilyl-2-thiapropyl)-3-(9-triethoxysilyl-3,4,5,6-tetrathianonyl)cyclohexyl]ethyl tetrasulfide; bis-2-[4-(3-triethoxysilyl-1-thiapropyl)-3-(9-triethoxysilyl-3,4,5,6-tetrathianonyl)cyclohexyl]ethyl trisulfide; bis-2-[4-(3-triethoxysilyl-1-thiapropyl)-3-(7-triethoxysilyl-3,4-dithiaheptyl)cyclohexyl]ethyl disulfide; bis-2-[4-(6-triethoxysilyl-3-thiahexyl)-3-(9-triethoxysilyl-3,4,5-trithianonyl)phenyl]ethyl tetrasulfide; bis-2-[4-(6-triethoxysilyl-3-thiahexyl)-3-(9-triethoxysilyl-3,4,5-trithianonyl)nathyl]ethyl tetrasulfide; bis-2-[4-(4-diethoxymethylsilyl-2-thiabutyl)-3-(9-triethoxysilyl-3,4,5,6-tetrathianonyl)phenyl]ethyl trisulfide; bis-2-[4-(4-triethoxysilyl-2-thiaethyl)-3-(7-triethoxysilyl-3,4-dithiaheptyl)cycloheptyl]ethyl disulfide; bis-2-[4-(4-triethoxysilyl-2-thiaethyl)-3-(7-triethoxysilyl-3,4-dithiaheptyl)cyclooctyl]ethyl disulfide; bis-2-[4-(4-triethoxysilyl-2-thiaethyl)-3-(7-triethoxysilyl-3,4-dithiaheptyl)cyclododecyl]ethyl disulfide; 4-(6-triethoxysilyl-3-thiahexyl)-1,2-bis-(9-triethoxysilyl-3,4,5,6-tetrathianonyl)cyclohexane; 2-(6-triethoxysilyl-3-thiahexyl)-1,4-bis-(9-triethoxysilyl-3,4,5,6-tetrathianonyl)cyclohexane; 1-(6-triethoxysilyl-3-thiahexyl)-2,4-bis-(9-triethoxysilyl-3,4,5,6-tetrathianonyl)cyclohexane; 4-(6-triethoxysilyl-3-thiahexyl)-1,2-bis-(7-triethoxysilyl-3,4-dithiaheptyl)cyclohexane; 2-(6-triethoxysilyl-3-thiahexyl)-1,4-bis-(7-triethoxysilyl-3,4-dithiaheptyl)cyclohexane; 1-(6-triethoxysilyl-3-thiahexyl)-2,4-bis-(7-triethoxysilyl-3,4-dithiaheptyl)cyclohexane.

In another embodiment of the present invention, the Formulae (1), (2) and (3), are described wherein each occurrence of $R^1$ and $R^3$ are independently selected from a divalent hydrocarbon fragment having from 1 to about 5 carbon atoms that include branched and straight chain alkyl, alkenyl, alkynyl, aryl or aralkyl groups in which one hydrogen atom was substituted with a $Y^1$ or $Y^2$ group; each occurrence of $Y^1$ and $Y^2$ is chosen independently from silyl (—$SiX^1X^2X^3$); each occurrence of $R^2$ is a straight chain hydrocarbon represented by —$(CH_2)_f$— where f is an integer from about 1 to about 5; each occurrence of $R^4$ is chosen independently from a polyvalent cyclic hydrocarbon fragment of 5 to about 12 carbon atom that was obtained by substitution of hydrogen atoms equal to the sum of a+c+e, and include cyclic alkyl, aryl and arenyl in which a+c+e−1 hydrogens have been replaced; each occurrence of $R^5$ is chosen independently from a polyvalent cyclic hydrocarbon fragment of 5 to about 12 carbon atom that was obtained by substitution of hydrogen atoms equal to the sum of a+c, and include cyclic alkyl, aryl and arenyl in which a+c−1 hydrogens have been replaced;

each occurrence of $X^1$ is chosen independently from the set of hydrolyzable groups consisting of —OH, —$OR^6$, in which $R^6$ is a monovalent hydrocarbon group having from 1 to 5 carbon atoms, and includes branched or straight chain alkyl, alkenyl, aryl or aralkyl groups; each occurrence of $X^2$ and $X^3$ is chosen independently taken from the group consisting of the members listed above for $R^6$, the members listed above for $X^1$ and —OSi containing groups that result from the condensation of silanols; each occurrence of the subscripts, a, b, c, d, e, f, m, n, o, p, and x, is independently given by a is 1 to about 2; b is 1 to about 3; c is 1; d is 1 to about 3; e is 1; f is 0 to about 5; m is 1, n is 1 to about 10; o is 0 to about 1; p is 1, and x is 1 to about 6.

In another embodiment, 30 to 99 weight percent of the silated cyclic core polysulfide of the present invention is blended with 70 to 1 weight percent of another silane, including silanes of the structure represented in Formula (4)

$$[X^1X^2X^3SiR^1S_xR^3SiX^1X^2X^3] \quad \text{(Formula 4)}$$

wherein each occurrence of each occurrence of $R^1$ and $R^3$ are chosen independently from a divalent hydrocarbon fragment having from 1 to about 20 carbon atoms that include branched and straight chain alkyl, alkenyl, alkynyl, aryl or aralkyl groups in which one hydrogen atom was substituted with independently a —$SiX^1X^2X^3$ group, wherein $X^1$ is chosen independently from the set of hydrolyzable groups consisting of —Cl, —Br, —OH, —$OR^6$, and $R^6C(=O)O$—, in which $R^6$ is any monovalent hydrocarbon group having from 1 to 20 carbon atoms, and includes branched or straight chain alkyl, alkenyl, aryl or aralkyl group and $X^2$ and $X^3$ is chosen independently taken from the group consisting of hydrogen, the members listed above for $R^6$, the members listed above for $X^1$ and —OSi containing groups that result from the condensation of silanols. Representative examples of the silane described by Formula 4 are listed in U.S. Pat. No. 3,842,111 and include bis-(3-triethoxysilylpropyl) disulfide; bis-(3-triethoxysilylpropyl) trisulfide; bis-(3-triethoxysilylpropyl) tetrasulfide, bis-(3-triethoxysilylpropyl) pentasulfide; bis-(3-diethoxymethylsilylpropyl) disulfide; bis-(3-ethoxydimethylsilylpropyl) disulfide; bis-(triethoxysilylmethyl) disulfide; bis-(4-triethoxysilylbenzyl) disulfide; bis-(3-triethoxysilylphenyl) disulfide and the like.

The bonding of sulfur to a methylene group on $R^4$ and $R^5$ is required because the methylene group mitigates excessive steric interactions between the silane and the filler and polymer. Two successive methylene groups mitigate steric interactions even further and also add flexibility to the chemical structure of the silane, thereby enhancing its ability to accommodate the positional and orientational constraints imposed by the morphologies of the surfaces of both the rubber and filler at the interphase, at the molecular level. The silane flexibility becomes increasingly important as the total number of silicon and sulfur atoms bound to $G^1$ and $G^2$ increases from 3 to 4 and beyond. Structures in which the polysulfide group is bonded directly to secondary and tertiary carbon atoms, ring structures, especially aromatic structures, are rigid and sterically hindered. The accelerators and curatives cannot readily orient themselves with the polysulfide group to affect reaction and the silated cyclic core polysulfide cannot readily orient itself to meet available binding sites on silica and polymer. This would tend to leave sulfur groups unbound to polymer, thereby reducing the efficiency by which the principle of multiple bonding of silane to polymer via multiple sulfur groups on silane, is realized.

The use of a sulfide group to attach the silyl group to the core, —S—$R^2SiX^1X^2X^3$, provides a convenient and cost effective way to bond the silyl group to the core. The sulfide group is less reactive than the polysulfide groups of the present invention and therefore is less likely to be broken during the curing of the rubbers containing the silated cyclic core polysulfides. The sulfide linkage of the silyl group to the core also makes it easier synthesize molecules with different lengths of the $R^2$ relative to $R^1$ and $R^3$ and therefore to optimize the chemical structure of the silated cyclic core polysulfides to achieve bonding between the inorganic filler, such as silica, and the rubber.

The function of the other silanes in the blend are to occupy sites on the surface of the silica which aid in dispersing the silica and coupling with the polymer.

Process for Preparing Silated Cyclic Core Polysulfides

In another embodiment of the present invention, the silated cyclic core polysulfides are prepared by (a) reacting a thioacid with the structure, $R^6C(=O)SH$ with a hydrocarbon containing reactive double bonds; (b) deblocking the mercapto group using a proton donator; (c) reacting the intermediate mercaptan in step b with a base and then a halo containing hydrocarbon silane; (d) reacting the intermediate mercapto silane from step c with a base and sulfur; (e) reacting the intermediate in step d with a substituted or unsubstituted hydrocarbon containing a leaving group selected from chlorine, bromine or iodine.

The structure of the hydrocarbon containing reactive double bonds in step (a) can be represented by the chemical structure shown if Formula (5)

(Formula 5)

wherein each occurrence is described supra and the subscripts g, h and i are independently given by g is about 0 to 3; h is 0 to about 3; and i is 0 to about 3.

The free radical reagent include oxidizing agents that are capable of converting the thiocarboxylic acid to a thiocarboxylic acid radical, i.e. $R^6C(=O)S\bullet$, and include, but are not limited to oxygen, peroxides, hydroperoxides, and the like.

The proton donor species are any hydrogen containing heterocarbon or substituted heterocarbon that is capable of reacting with the thiocarboxylic acid ester intermediate in step (c) to generate an unblocked mercaptan. Representative examples of these hydrogen donor species include alcohols, such as methanol, ethanol, isopropyl alcohol, propanol, and the like; amines such as ammonia, methyl amine, propyl amine, diethanol amine, and the like; mercaptans, such as propyl mercaptans, butyl mercaptan, and the like.

The structure of the substituted or unsubstituted hydrocarbon containing a leaving group used in step (e) is represented by Formulae (6) and (7)

$$Y^1R^1Z \quad \text{(Formula 6)}$$

$$Y^2R^3Z \quad \text{(Formula 7)}$$

wherein each occurrence of $Y^1$, $Y^2$, $R^1$, and $R^2$ are as previously defined and Z is selected from the group Cl, Br and I.

The structure of the halo containing hydrocarbon silane used in step (c) is represented by Formula (8)

$$ZR^2SiX^1X^2X^3 \quad \text{(Formula 8)}$$

wherein each occurrence of $R^2$, $X^1$, $X^2$ and $X^3$ are as previously defined and Z is selected from the group Cl, Br and I.

The reaction may be carried in the presence or absence of organic solvents, including methanol, ethanol, isopropyl alcohol, tetrahydrofuran, diethyl ether, hexanes, cyclohexane, toluene, xylenes, and the like.

Use in Rubber Compositions

In one embodiment of the present invention, a rubber composition comprising:
 (a) the silated cyclic core polysulfide of the present invention (Formula 1);
 (b) inorganic filler; and,
 (c) rubber.

In another embodiment of the present invention, a cured rubber composition comprising:
 (a) The silated cyclic core polysulfide of the present invention (Formula 1)$_r$;
 (b) inorganic filler;
 (c) rubber;
 (d) curatives; and,
 (e) optionally, other additives.

The rubbers useful with the coupling agents described herein include sulfur vulcanizable rubbers including conjugated diene homopolymers and copolymers, and copolymers of at least one conjugated diene and aromatic vinyl compound. Suitable organic polymers for preparation of rubber compositions are well known in the art and are described in various textbooks including *The Vanderbilt Rubber Handbook*, Ohm, R. F., R.T. Vanderbilt Company, Inc., 1990 and in the *Manual for the Rubber Industry*, Kemperman, T. and Koch, S. Jr., Bayer AG, LeverKusen, 1993.

One example of a suitable polymer for use herein is solution-prepared styrene-butadiene rubber (sSBR). In one embodiment of the invention, the solution prepared sSBR has a bound styrene content in a range of about 5 to about 50 weight percent. In another embodiment of the invention, the solution prepared sSBR has a bound styrene content in a range of about 9 to about 36 weight percent. Other useful polymers include emulsion-prepared styrene-butadiene rubber (eSBR), natural rubber (NR), ethylene-propylene copolymers and terpolymers (EP, EPDM), acrylonitrile-butadiene rubber (NBR), polybutadiene (BR), and so forth.

In another embodiment, the rubber composition is comprised of at least one diene-based elastomer, or rubber. Suitable conjugated dienes include, but are not limited to, isoprene and 1,3-butadiene and suitable vinyl aromatic compounds include, but are not limited to, styrene and alpha methyl styrene. Polybutadiene may be characterized as existing primarily, typically about 90% by weight, in the cis-1,4-butadiene form, but other compositions may also be used for the purposes described herein.

Thus, the rubber is a sulfur curable rubber. Such diene based elastomer, or rubber, may be selected, for example, from at least one of cis-1,4-polyisoprene rubber (natural and/or synthetic), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization prepared styrene/butadiene/acrylonitrile terpolymer rubber and butadiene/acrylonitrile copolymer rubber. In one embodiment of the invention, an emulsion polymerization derived styrene/butadiene (eSBR) having a relatively conventional styrene content of about 20 to about 28 percent bound styrene is used. In another embodiment, an eSBR having a medium to relatively high bound styrene content of about 30 to about 45 percent may be used.

Emulsion polymerization prepared styrene/butadiene/acrylonitrile terpolymer rubbers containing from about 2 to about 40 weight percent bound acrylonitrile in the terpolymer are also contemplated as diene based rubbers for use in this invention.

A particulate filler may also be added to the crosslinkable elastomer compositions of the present invention including siliceous fillers, carbon black, and so forth. The filler materials useful herein include, but are not limited to, metal oxides such as silica (pyrogenic and/or precipitated), titanium dioxide, aluminosilicate and alumina, clays and talc, carbon black, and so forth.

Particulate, precipitated silica is also sometimes used for such purpose, particularly when the silica is used in conjunction with a silane. In some cases, a combination of silica and carbon black is utilized for reinforcing fillers for various rubber products, including treads for tires. Alumina can be used either alone or in combination with silica. The term, alumina, can be described herein as aluminum oxide, or $Al_2O_3$. The fillers may be hydrated or in anhydrous form.

The silated cyclic core polysulfide silane(s) may be premixed or pre-reacted with the filler particles, or added to the rubber mix during the rubber and filler processing, or mixing stages. If the silated cyclic core polysulfide silanes and filler are added separately to the rubber mix during the rubber and filler mixing, or processing stage, it is considered that the silated cyclic core polysulfide silane(s) then combine(s) in an in-situ fashion with the filler.

The vulcanized rubber composition should contain a sufficient amount of filler to contribute a reasonably high modulus and high resistance to tear. In one embodiment of the present invention, the combined weight of the filler may be as low as about 5 to about 100 parts by weight per hundred parts rubber (phr). In another embodiment, the combined weight of the filler is from about 25 to about 85 phr and at least one precipitated silica is utilized as a filler. The silica may be characterized by having a BET surface area, as measured using nitrogen gas, in the range of about 40 to about 600 m$^2$/g. In another embodiment of the invention, the silica has a BET surface area in a range of about 50 to about 300 m$^2$/g. The BET method of measuring surface area is described in the *Journal of the American Chemical Society*, Volume 60, page 304 (1930). The silica typically may also be characterized by having a dibutylphthalate (DBP) absorption value in a range of about 100 to about 350, and more usually about 150 to about 300. Further, the silica, as well as the aforesaid alumina and aluminosilicate, may be expected to have a CTAB surface area in a range of about 100 to about 220. The CTAB surface area is the external surface area as evaluated by cetyl trimethylammonium bromide with a pH of about 9. The method is described in ASTM D 3849.

Mercury porosity surface area is the specific surface area determined by mercury porosimetry. Using this method, mercury is penetrated into the pores of the sample after a thermal treatment to remove volatiles. Set up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, p. 39 (1959) or according to DIN 66133. For such an evaluation, a CARLO-ERBA Porosimeter 2000 might be used. The average mercury porosity specific surface area for the silica should be in a range of 100 to 300 m$^2$/g.

In one embodiment of the invention, a suitable pore size distribution for the silica, alumina and aluminosilicate according to such mercury porosity evaluation is considered herein to be such that five percent or less of its pores have a diameter of less than about 10 nm, about 60 to about 90 percent of its pores have a diameter of about 10 to about 100 nm, about 10 to about 30 percent of its pores have a diameter at about 100 to about 1,000 nm, and about 5 to about 20 percent of its pores have a diameter of greater than about 1,000 nm.

In another embodiment, the silica might be expected to have an average ultimate particle size, for example, in the range of about 10 to about 50 nm as determined by the electron microscope, although the silica particles may be even smaller, or possibly larger, in size. Various commercially available silicas may be considered for use in this invention such as, from PPG Industries under the HI-SIL trademark with designations HI-SIL 210, 243, etc.; silicas available from Rhone-Poulenc, with, for example, designation of ZEO-SIL 1165 MP; silicas available from Degussa with, for example, designations VN2 and VN3, etc. and silicas commercially available from Huber having, for example, a designation of HUBERSIL7 8745.

In still another embodiment, the compositions may utilize siliceous fillers such as silica, alumina and/or aluminosilicates in combination with carbon black reinforcing pigments. The compositions may comprise a filler mix of about 15 to about 95 weight percent of the siliceous filler, and about 5 to about 85 weight percent carbon black, wherein the carbon black has a CTAB value in a range of 80 to 150. More typically, it is desirable to use a weight ratio of siliceous fillers to carbon black of at least about 3/1, and preferably at least about 10/1. The weight ratio may range from about 3/1 to about 30/1 for siliceous fillers to carbon black.

In another embodiment, the filler can be comprised of about 60 to about 95 weight percent of said silica, alumina and/or aluminosilicate and, correspondingly, about 40 to about 5 weight percent carbon black. The siliceous filler and carbon black may be pre-blended or blended together in the manufacture of the vulcanized rubber.

In yet another embodiment of the present invention, the rubber compositions of the present invention are prepared by mixing one or more of the silated cyclic core polysulfide silanes with the organic polymer before, during or after the compounding of the filler into the organic polymer. In another embodiment, the silated cyclic core polysulfide silanes are added before or during the compounding of the filler into the organic polymer, because these silanes facilitate and improve the dispersion of the filler. In another embodiment, the total amount of silated cyclic core polysulfide silane present in the resulting combination should be about 0.05 to about 25 parts by weight per hundred parts by weight of rubber (phr); and 1 to 10 phr in another embodiment. In yet another embodiment, fillers can be used in quantities ranging from about 5 to about 100 phr, and still in another embodiment from about 25 to about 80 phr.

In practice, sulfur vulcanized rubber products typically are prepared by thermomechanically mixing rubber and various ingredients in a sequentially step-wise manner followed by shaping and curing the compounded rubber to form a vulcanized product. First, for the aforesaid mixing of the rubber and various ingredients, typically exclusive of sulfur and sulfur vulcanization accelerators (collectively, curing agents), the rubber(s) and various rubber compounding ingredients typically are blended in at least one, and often (in the case of silica filled low rolling resistance tires) two or more, preparatory thermomechanical mixing stage(s) in suitable mixers. Such preparatory mixing is referred to as nonproductive mixing or non-productive mixing steps or stages. Such preparatory mixing usually is conducted at temperatures of about 140° C. to 200° C., and for some compositions, about 150° C. to 180° C. Subsequent to such preparatory mixing stages, in a final mixing stage, sometimes referred to as a productive mixing stage, curing agents, and possibly one or more additional ingredients, are mixed with the rubber compound or composition, at lower temperatures of typically about 50° C. to 130° C. in order to prevent or retard premature curing of the sulfur curable rubber, sometimes referred to as scorching. The rubber mixture, also referred to as a rubber compound or composition, typically is allowed to cool, sometimes after or during a process intermediate mill mixing, between the aforesaid various mixing steps, for example, to a temperature of about 50° C. or lower. When it is desired to mold and to cure the rubber, the rubber is placed into the appropriate mold at a temperature of at least about 130° C. and up to about 200° C. which will cause the vulcanization of the rubber by the S—S bond-containing groups (i.e., disulfide, trisulfide, tetrasulfide, etc.; polysulfide) on the silated cyclic core polysulfide silanes and any other free sulfur sources in the rubber mixture.

Thermomechanical mixing refers to the phenomenon whereby under the high shear conditions in a rubber mixer, the shear forces and associated friction occurring as a result of mixing the rubber compound, or some blend of the rubber compound itself and rubber compounding ingredients in the high shear mixer, the temperature autogeneously increases, i.e. it "heats up". Several chemical reactions may occur at various steps in the mixing and curing processes.

The first reaction is a relatively fast reaction and is considered herein to take place between the filler and the silicon alkoxide group of the silated cyclic core polysulfides. Such reaction may occur at a relatively low temperature such as, for example, at about 120° C. The second reaction is considered herein to be the reaction which takes place between the sulfur-containing portion of the silated cyclic core polysulfide silane, and the sulfur vulcanizable rubber at a higher temperature; for example, above about 140° C.

Another sulfur source may be used, for example, in the form of elemental sulfur, such as but not limited to $S_8$. A sulfur donor is considered herein as a sulfur containing compound which liberates free, or elemental sulfur, at a temperature in a range of 140° C. to 190° C. Such sulfur donors may be, for example, although are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid silated cyclic core polysulfide silane. Thus, for example, the independent addition of a sulfur source may be manipulated by the amount of addition thereof and by the sequence of addition relative to the addition of other ingredients to the rubber mixture.

In one embodiment of the invention, the rubber composition may therefore comprise about 100 parts by weight of at least one sulfur vulcanizable rubber selected from the group consisting of conjugated diene homopolymers and copolymers, and copolymers of at least one conjugated diene and aromatic vinyl compound, about 5 to about 100 parts, preferably about 25 to about 80 parts per hundred parts by weight per 100 parts by weight rubber of at least one particulate filler, up to about 5 parts by weight per 100 parts by weight rubber of a curing agent, and about 0.05 to about 25 parts per hundred parts of polymer of at least one silated cyclic core polysulfide silane as described in the present invention.

In another embodiment of the present invention, the filler comprises from about 1 to about 85 weight percent carbon black based on the total weight of the filler and 0 to about 20 parts by weight of at least one silated cyclic core polysulfide silane based on the total weight of the filler.

In still another embodiment, the rubber composition is prepared by first blending rubber, filler and silated cyclic core polysulfide silane, or rubber, filler pretreated with all or a portion of the silated cyclic core polysulfide silane and any remaining silated cyclic core polysulfide silane, in a first thermomechanical mixing step to a temperature of about 140° C. to about 200° C. for about 2 to about 20 minutes. In another embodiment, filler pretreated with all or a portion of the silated cyclic core polysulfide silane and any remaining silated cyclic core polysulfide silane, in a first thermomechanical mixing step to a temperature of about 140° C. to about 209° C. for about 4 to 15 minutes. Optionally, the curing agent is then added in another thermomechanical mixing step at a temperature of about 50° C. and mixed for about 1 to about 30 minutes. The temperature is then heated again to between about 130° C. and about 200° C. and curing is accomplished in about 5 to about 60 minutes.

In another embodiment, the process may also comprise the additional steps of preparing an assembly of a tire or sulfur vulcanizable rubber with a tread comprised of the rubber composition prepared according to this invention and vulcanizing the assembly at a temperature in a range of 130° C. to 200° C.

Other optional ingredients may be added in the rubber compositions of the present invention including curing aids, i.e. sulfur compounds, including activators, retarders and accelerators, processing additives such as oils, plasticizers, tackifying resins, silicas, other fillers, pigments, fatty acids, zinc oxide, waxes, antioxidants and antiozonants, peptizing agents, reinforcing materials such as, for example, carbon black, and so forth. Such additives are selected based upon the intended use and on the sulfur vulcanizable material selected for use, and such selection is within the knowledge of one of skill in the art, as are the required amounts of such additives known to one of skill in the art.

The vulcanization may be conducted in the presence of additional sulfur vulcanizing agents. Examples of suitable sulfur vulcanizing agents include, for example elemental sulfur (free sulfur) or sulfur donating vulcanizing agents, for example, an amino disulfide, polymeric polysulfide or sulfur olefin adducts which are conventionally added in the final, productive, rubber composition mixing step. The sulfur vulcanizing agents, which are common in the art are used, or added in the productive mixing stage, in an amount ranging from about 0.4 to about 3 phr, or even, in some circumstances, up to about 8 phr, with a range of from about 1.5 to about 2.5 phr and all subranges therebetween in one embodiment from 2 to about 2.5 phr and all subranges therebetween in another embodiment.

Optionally, vulcanization accelerators, i.e., additional sulfur donors, may be used herein. It is appreciated that they may be, for example, of the type such as, for example, benzothiazole, alkyl thiuram disulfide, guanidine derivatives and thiocarbamates. Representative of such accelerators are, for example, but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis (dibenzyl amine). Other additional sulfur donors, may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2, N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally, a primary accelerator(s) is used in total amounts ranging from about 0.5 to about 4 and all subranges therebetween in one embodiment, and from about 0.8 to about 1.5, phr and all subranges therebetween in another embodiment. Combinations of a primary and a secondary accelerator might be used with the secondary accelerator being used in smaller amounts (of about 0.05 to about 3 phr and all subranges therebetween) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator can be a guanidine, dithiocarbamate or thiuram compound.

Typical amounts of tackifier resins, if used, comprise about 0.5 to about 10 phr and all subranges therebetween, usually about 1 to about 5 phr and all subranges therebetween. Typical amounts of processing aids comprise about 1 to about 50 phr and all subranges therebetween. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344-346. Typical amounts of antiozonants, comprise about 1 to about 5 phr and all subranges therebetween. Typical amounts of fatty acids, if used, which can include stearic acid, comprise about 0.5 to about 3 phr and all subranges therebetween. Typical amounts of zinc oxide comprise about 2 to about 5 phr. Typical amounts of waxes comprise about 1 to about 5 phr and all subranges therebetween. Often microcrystalline waxes are used. Typical amounts of peptizers comprise about 0.1 to about 1 phr and all subranges therebetween. Typical peptizers may be, for example, pentachlorothiophenol and dibenzamidodiphenyl disulfide.

The rubber compositions of this invention can be used for various purposes. For example, it can be used for various tire compounds, weather stripping, and shoe soles. In one embodiment of the present invention, the rubber compositions described herein are particularly useful in tire treads, but may also be used for all other parts of the tire as well. The tires can be built, shaped, molded and cured by various methods that are known and will be readily apparent to those having skill in such art.

In another embodiment, the silated cyclic core polysulfide of the present invention may be loaded on a carrier, or filler, such as, for example, a porous polymer, carbon black, silica or the like, so that they are in a dry free flowing form for convenient delivery to rubber. In one embodiment, the carrier would be part of the inorganic filler to be used in the rubber.

In one embodiment of the invention, a dry free flowing composition comprises the silated cyclic core polysulfides in accordance with this invention in admixture with one or more of the aforesaid carrier materials, e.g., in a weight ratio of from about 0.1 to about 60 weight percent. The BET surface area of such carriers as silica can vary widely and in one embodiment can vary from about 100 m$^2$/g to about 300 m$^2$/g. Another property of such carriers is their DOP adsorption, an oil adsorption index. In the case of nonporous carriers such as silica, the DOP adsorption can range from about 100 ml/100 gm to about 400 ml/100 gm. Porous carriers such as foamed polyolefins can advantageously absorb from about 10 ml to about 250 ml/100 gm (from about 9 to about 70 weight percent) of the silane of the present invention.

The filler can be essentially inert to the silane with which it is admixed as is the case with carbon black or organic polymers, or it can be reactive therewith, e.g., the case with carriers possessing metal hydroxyl surface functionality, e.g., silicas and other silaceous particulates which possess surface silanol functionality.

EXAMPLES

The examples presented below demonstrate significant advantages of the silanes described herein relative those of the currently practiced art, in their performance as coupling agents in silica-filled rubber.

Example 1

Preparation of (6-triethoxysilyl-3-thia-1-hexyl)-bis-(7-triethoxysilyl-3,4-dithiaheptyl)cyclohexane, related oligomers and bis-(3-triethoxysilylpropyl) polysulfide mixture This example illustrates the preparation of a silated cyclic core disulfide from a core containing three vinyl groups through the formation of an intermediate thioacetate silane. The tris-(4-oxo-3-thiapentyl)cyclohexane was prepared by the reaction of thioacetic acid with trivinylcyclohexane. Into a 5 L, three-neck round bottomed flask equipped with magnetic stir bar, temperature probe/controller, heating mantle, addition funnel, condenser, and air inlet were charged 1,2,4-trivinylcyclohexane (779 grams, 4.8 moles) and t-butyl peroxide (8.0 grams, 0.055 mole). Freshly distilled thioacetic acid (1297 grams, 16.8 moles) was added by means of an addition funnel over a period of 30 minutes. The temperature rose from room temperature to 59° C. The reaction mixture was allowed to cool to room temperature, tert-butyl peroxide (25.3 grams, 0.173 moles) was added in two increments and the reaction mixture was heated overnight at 75° C. After cooling to 42° C., air was bubbled into the reaction mixture and an exotherm was observed. The mixture was stirred overnight at 75° C. and then cooled to room temperature. The reaction mixture was stripped to remove any low boiling species under reduced pressure and a maximum temperature of 135° C. to give the final product (1,866 grams, 4.77 moles). The yield was 99 percent.

The 1,2,4-tris-(2-mercaptoethyl)cyclohexane was prepared by removing the acyl group. Into a 5 L, three-neck round bottomed flask equipped with magnetic stir bar, temperature probe/controller, heating mantle, addition funnel, distilling head and condenser, and nitrogen inlet were charged tris-(4-oxo-3-thiapentyl)cyclohexane (1,866 grams, 4.77 moles) and absolute ethanol (1,219 grams, 26.5 moles). Sodium ethoxide in ethanol (99 grams of 21% sodium ethoxide, purchased from Aldrich Chemical) was added in five increments. The mixture was heated and the ethanol and ethyl acetate were removed. Ethanol (785 grams) was added and the ethyl acetate and ethanol were distilled from the mixture at atmospheric pressure. Ethanol (1,022 grams) was added to the mixture and the ethyl acetate, ethanol and low boiling components were distilled form the mixture under reduced pressure at 73° C. The mercaptan intermediate (1,161 grams, 4.5 moles) was used in the next step for the synthesis. The yield was 93 percent.

The bis-(2-mercaptoethyl)(6-triethylsilyl-3-thia-1-hexyl) cyclohexane was prepared by reaction of the trimercaptan intermediate with 3-chloropropyltriethyoxysilane. Into a 3 L, three-neck round bottomed flask equipped with magnetic stir bar, temperature probe/controller, heating mantle, addition funnel, condenser, air inlet and a sodium hydroxide scrubber, was charged 1,2,4-tris-(2-mercaptoethyl)cyclohexane (450 grams, 1.7 moles). Sodium ethoxide in ethanol (421 grams of 21% sodium ethoxide, purchased from Aldrich Chemical) was added over two hours. 3-Chloropropyltriethoxysilane (410 grams, 1.7 moles) was added slowly over a period of 2 hours and then heated at reflux for 14 hours. An additional aliquot of 3-chloropropyltriethoxysilane (42.5 grams, 0.18 mole) was added, heated for 2.5 hours at 79° C., cooled and then filtered. The crude product was distilled under reduced pressure. The fraction that boiled between 191 and 215° C. was collected (343 grams, 0.73 mole) and used in the next step of the synthesis. The product yield was 43 percent.

Figure 1:
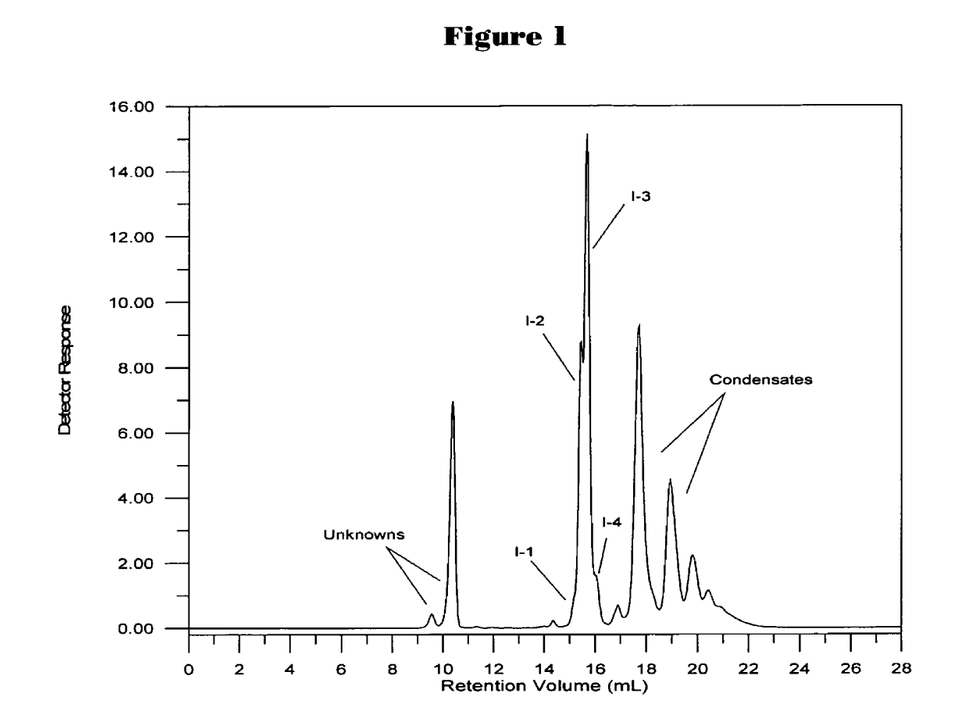
FIG. 1 shows HPLC analysis of the product of Example 1.

The product, (6-triethoxysilyl-3-thia-1-hexyl)-bis-(7-triethoxysilyl-3,4-dithiaheptyl)cyclohexane, was prepared by reacting the silated dimercaptan intermediated with sulfur and 3-chloropropyltriethoxysilane. Into a 3 L, three-neck round bottomed flask equipped with magnetic stir bar, temperature probe/controller, heating mantle, addition funnel, distilling head and condenser, and nitrogen inlet were charged bis-(2-mercaptoethyl)(6-triethylsilyl-3-thia-1-hexyl)cyclohexane (326 grams, 0.7 mole), sodium ethoxide in ethanol (451 grams of 21% sodium ethoxide, purchased from Aldrich Chemical), sulfur powder (45 grams, 1.4 moles) and absolute ethanol (352 grams) and refluxed for 3 hours. 3-Chloropropyltriethoxysilane (336 grams, 1.4 moles) was added, refluxed for 72 hours, cooled and filtered using a glass fritted filter with a 25-50 micron pore size. The solids were washed with toluene, the organic layers combined and stripped to remove the lights. The final product (635 grams, 0.7 mole) was analyzed by HPLC. The chromatograph, shown in FIG. 1, indicated a mixture of monomeric and oligomeric products.

Example 2

Preparation of (6-triethoxysilyl-3-thia-1-hexyl)-bis-(9-triethoxysilyl-3,4,5,6-tetrathianonyl)cyclohexane, related oligomers and bis-(3-triethoxysilylpropyl) polysulfide mixture The dimercaptan silane intermediate, (6-triethoxysilyl-3-thia-1-hexyl)-bis-(2-mercaptoethyl)cyclohexane, was prepared by the procedure described in Example 1.

The product, (6-triethoxysilyl-3-thia-1-hexyl)-bis-(9-triethoxysilyl-3,4,5,6-tetrathianonyl)cyclohexane, related oligomers and bis-(3-triethoxysilylpropyl)polysulfide mixture, was prepared by reacting the dimercaptan silane with base, sulfur and 3-chloropropyltriethoxysilane. Into a 2 L, three-neck round bottomed flask equipped with magnetic stir bar, temperature probe/controller, heating mantle, addition funnel, distilling head and condenser, and nitrogen inlet were charged bis-(2-mercaptoethyl)(6-triethylsilyl-3-thia-1-hexyl)cyclohexane (249.7 grams, 0.53 mole), sodium ethoxide in ethanol (345.2 grams of 21% sodium ethoxide, purchased from Aldrich Chemical), sulfur powder (102.5 grams, 3.2 moles) and absolute ethanol (250 grams) and refluxed for 24 hours. 3-Chloropropyltriethoxysilane (256.5 grams, 1.07 moles) was added, refluxed for 72 hours, cooled and then filtered using a 3.5 micron asbestocel filter. The final product (487.4 grams, 0.47 mole, 88 percent yield) was analyzed by HPLC. The chromatograph indicated a mixture of products.

Comparative Example A-C, Examples 3-5

The Use of Silanes in Low Rolling Resistant Tire Tread Formulation

A model low rolling resistance passenger tire tread formulation as described in Table 1 and a mix procedure were used to evaluate representative examples of the silanes of the present invention. The silane in Example 2 was mixed as follows in a "B" BANBURY® (Farrell Corp.) mixer with a 103 cu. in. (1,690 cc) chamber volume. The mixing of the rubber was done in two steps. The mixer was turned on with the mixer at 80 rpm and the cooling water at 71° C. The rubber polymers were added to the mixer and ram down mixed for 30 seconds. The silica and the other ingredients in Masterbatch of Table 1 except for the silane and the oils were added to the mixer and ram down mixed for 60 seconds. The mixer speed was reduced to 35 rpm and then the silane and oils of the Materbatch were added to the mixer and ram down for 60 seconds. The mixer throat was dusted down and the ingredients ram down mixed until the temperature reached 149° C. The ingredients were then mixed for an addition 3 minutes and 30 seconds. The mixer speed was adjusted to hold the temperature between 152 and 157° C. The rubber was dumped (removed from the mixer), a sheet was formed on a roll mill set at about 85° to 88° C., and then allowed to cool to ambient temperature.

In the second step, Masterbatch was recharged into the mixer. The mixer's speed was 80 rpm, the cooling water was set at 71° C. and the batch pressure was set at 6 MPa. The Masterbatch was ram down mixed for 30 seconds and then the temperature of the Masterbatch was brought up to 149° C., and then the mixer's speed was reduce to 32 rpm and the rubber was mixed for 3 minutes and 20 seconds at temperatures between 152 and 157° C. After mixing, the rubber was dumped (removed from the mixer), a sheet was formed on a roll mill set at about 85° to 88° C., and then allowed to cool to ambient temperature.

The rubber Masterbatch and the curatives were mixed on a 15 cm×33 cm two roll mill that was heated to between 48° and 52° C. The sulfur and accelerators were added to the rubber (Masterbatch) and thoroughly mixed on the roll mill and allowed to form a sheet. The sheet was cooled to ambient conditions for 24 hours before it was cured. The curing condition was 160° C. for 20 minutes. The silated cyclic core polysulfides from Examples 1 and 2 were compounded into the tire tread formulation according to the above procedure and their performance was compared to the performance of silanes which are practiced in the prior art, bis-(3-triethoxysilyl-1-propyl)disulfide (TESPD), bis-(3-triethoxysilyl-1-propyl) tetrasulfide (TESPT) and 1,2,4-tris-(7-triethoxysilyl-3,4-dithiaheptyl)cyclohexane (TESHC), Comparative Examples A-C. The test procedures were described in the following ASTM methods:

| | |
|---|---|
| Mooney Scorch | ASTM D1646 |
| Mooney Viscosity | ASTM D1646 |
| Oscillating Disc Rheometer (ODR) | ASTM D2084 |
| Storage Modulus, Loss Modulus, Tensile and Elongation | ASTM D412 and D224 |
| DIN Abrasion | DIN Procedure 53516 |
| Heat Buildup | ASTM D623 |
| Percent Permanent Set | ASTM D623 |
| Shore A Hardness | ASTM D2240 |

The results of this procedure are tabulated below in Table 1.

TABLE 1

| Ingredients | Units | Comp. Ex. A | Comp. Ex B | Comp. Ex. C | Example 3 | Example 4 | Example 5 |
|---|---|---|---|---|---|---|---|
| Masterbatch | | | | | | | |
| SMR-10, natural rubber | phr | 10.00 | 10.00 | 10.00 | 10.00 | 10.00 | 10.00 |
| Budene 1207, polybutadiene | phr | 35.00 | 35.00 | 35.00 | 35.00 | 35.00 | 35.00 |
| Buna VSL 5025-1, oil-ext. sSBR | phr | 75.63 | 75.63 | 75.63 | 75.63 | 75.63 | 75.63 |
| N339, carbon black | phr | 12.00 | 12.00 | 12.00 | 12.00 | 12.00 | 12.00 |
| Ultrasil VN3 GR, silica | phr | 85.00 | 85.00 | 85.00 | 85.00 | 85.00 | 85.00 |
| Sundex 8125TN, process oil. | phr | 6.37 | 6.37 | 6.37 | 6.37 | 6.37 | 6.37 |
| Erucical H102, rapeseed oil | phr | 5.00 | 5.00 | 5.00 | 5.00 | 5.00 | 5.00 |
| Flexzone 7P, antiozonant | phr | 2.00 | 2.00 | 2.00 | 2.00 | 2.00 | 2.00 |
| TMQ | phr | 2.00 | 2.00 | 2.00 | 2.00 | 2.00 | 2.00 |
| Sunproof Improved, wax | phr | 2.50 | 2.50 | 2.50 | 2.50 | 2.50 | 2.50 |
| Kadox 720C, zinc oxide | phr | 2.50 | 2.50 | 2.50 | 2.50 | 2.50 | 2.50 |
| Industrene R, stearic acid | phr | 1.00 | 1.00 | 1.00 | 1.00 | 1.00 | 1.00 |
| Aktiplast ST, disperser | phr | 4.00 | 4.00 | 4.00 | 4.00 | 4.00 | 4.00 |
| Silane TESPD | phr | 6.00 | | | | | |
| Silane TESPT | phr | | 6.80 | | | | |
| Silane TESHC | phr | — | | 8.20 | | | |
| Silane, Example 1 | phr | | | | 7.90 | | |
| Silane, Example 2 | phr | | | | | 6 | 9 |
| Catalysts | | | | | | | |
| Naugex MBT | phr | 0.10 | 0.10 | 0.10 | 0.10 | 0.10 | 0.10 |
| CBS | phr | 2.00 | 2.00 | 2.00 | 2.00 | 2.00 | 2.00 |

TABLE 1-continued

| Ingredients | Units | Comp. Ex. A | Comp. Ex B | Comp. Ex. C | Example 3 | Example 4 | Example 5 |
|---|---|---|---|---|---|---|---|
| Diphenyl guanidine | phr | 2.00 | 2.00 | 2.00 | 2.00 | 2.00 | 2.00 |
| Rubbermakers sulfur 167 | phr | 2.20 | 2.20 | 2.20 | 2.20 | 2.20 | 2.20 |
| Rubber Properties | | | | | | | |
| Mooney Properties | | | | | | | |
| Viscosity at 100° C., ML1 + 4 | Mooney units | 70 | 75 | 67 | 68 | 68.2 | 68.7 |
| MV at 135° C., MS1+ | mooney units | 32.4 | 37 | 30 | 34.6 | 33.2 | 34.5 |
| Scorch at 135° C., MS1 + $t_3$ | min. | 14.2 | 8.1 | 13.2 | 7.3 | 8.1 | 5 |
| Cure at 135° C. MS1 + $t_{18}$ | min. | 18.5 | 13.3 | 17.1 | 11.3 | 13.3 | 9.5 |
| Rheometer (ODR) Properties, 1° arc at 149° C. | | | | | | | |
| $M_L$ | dN-m | 8.9 | 10.1 | 8.4 | 8.6 | 8.6 | 9.1 |
| $M_H$ | dN-m | 34.9 | 38.9 | 38.5 | 35.9 | 32.9 | 37.9 |
| t90 | min. | 18 | 17.1 | 14.5 | 11.5 | 17.4 | 13.5 |
| Physical Properties, cured to t90 at 149° C. | | | | | | | |
| Durometer Shore "A" | shore A | 66 | 69 | 68 | 66 | 66 | 69 |
| 100% Modulus | MPa | 2.35 | 2.8 | 2.56 | 2.72 | 2.38 | 2.89 |
| 300% Modulus | MPa | 8.54 | 10.86 | 9.06 | 11.42 | 9.79 | 12.32 |
| Reinforcement Index | | 3.63 | 3.88 | 3.54 | 4.2 | 4.11 | 4.26 |
| Tensile | MPa | 18.95 | 18.19 | 16.97 | 21.57 | 22.36 | 22.13 |
| Elongation | % | 582 | 448 | 492 | 505 | 590 | 500 |
| Abrasion (DIN) | mm$^3$ | 144 | 145 | 158 | 132 | 138 | 135 |
| Dynamic Properties in cured state, 60° C., simple shear - non-linearity (0-10%) | | | | | | | |
| $G'_{initial}$ | MPa | 8.1 | 7.7 | 9 | 4.7 | 6.91 | 6.2 |
| $\Delta G'$ | MPa | 5.8 | 5.2 | 6.5 | 2.65 | 4.65 | 3.87 |
| $G''_{max}$ | MPa | 1 | 0.91 | 1.07 | 0.53 | 0.786 | 0.66 |
| $\tan\delta_{max}$ | | 0.243 | 0.228 | 0.243 | 0.186 | 0.206 | 0.189 |
| Wet-skid indicator, 10 Hz, 1% DSA | | | | | | | |
| $\tan\delta | 0°$ C. | | | 0.243 | 0.34 | 0.34 | | 0.318 |

TESPD = bis-(3-triethoxysilylpropyl) disulfide
TESPT = bis(3-triethoxysilypropyl) tetrasulfide
TESHC = 1,2,4-tris-(3-triethoxysilyl-3,4-dithiaheptyl)cyclohexane Table 1, listed in Examples 3-5, presents the performance parameters of hydrocarbon core polysulfide silanes of the present invention, bis-(3-triethoxysilylpropyl) disulfide and bis-(3-triethoxysilylpropyl)tetrasulfide and 1,2,4-tris(6-triethoxysilyl-3,4-dithiaheptyl)cyclohexane.

The physical properties of the rubber compounded with silated cyclic core polysulfides from Examples 1 and 2 are consistently and substantially higher than the control silanes.

The silated cyclic core polysulfide of the present invention impart higher performance to silica-filled elastomer compositions, including better coupling of the silica to the rubber, as illustrated by the higher reinforcement index. The better reinforcing indices translate into performance improvements for the elastomer compositions and articles manufactured from these elastomers.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

The invention claimed is:

1. A silated cyclic core polysulfide of the general formula wherein:
each occurrence of $G^1$ is independently selected from a polyvalent hydrocarbon species having from 5 to about 30 carbon atoms containing a polysulfide group represented by the general formula:

each occurrence of $G^2$ is independently selected from a polyvalent hydrocarbon species of 3 to about 30 carbon atoms containing a polysulfide group represented by the general formula:

each occurrence of $R^1$ and $R^3$ is independently selected from a divalent hydrocarbon fragment having from 1 to about 20 carbon atoms;

each occurrence of $Y^1$ and $Y^2$ is independently selected from the group consisting of silyl ($-SiX^1X^2X^3$), alkoxy ($-OR^6$), hydrogen, carboxylic acid, ester ($-C(=O)OR^6$) wherein $R^6$ is a monovalent hydrocarbon group having from 1 to 20 carbon atoms;

each occurrence of $R^2$ is independently selected from divalent hydrocarbon fragment having from 1 to 20 carbon atoms;

each occurrence of $R^4$ is independently selected from a polyvalent cyclic hydrocarbon fragment of 3 to about 28 carbon atoms or a polyvalent cyclic heterocarbon fragment of 3 to about 27 carbon atoms that was obtained by substitution of hydrogen atoms equal to the sum of a +c+e;

each occurrence of $R^5$ is independently selected from a polyvalent hydrocarbon fragment of 1 to about 28 carbon atoms or a polyvalent cyclic heterocarbon fragment of 1 to about 27 carbon atoms that was obtained by substitution of hydrogen atoms equal to the sum of c+e;

each occurrence of $X^1$ is independently selected from the group consisting of —Cl, —Br, —OH, —$OR^6$, and $R^6C(=O)O$—, wherein $R^6$ is a monovalent hydrocarbon group having from 1 to 20 carbon atoms;

each occurrence of $X^2$ and $X^3$ is independently selected from the group consisting of hydrogen, $R^6$, wherein $R^6$ is a monovalent hydrocarbon group having from 1 to 20 carbon atoms, $X^1$, wherein $X^1$ is independently selected from the group consisting of —Cl, —Br, —OH, —$OR^6$, and $R^6C(=O)O$—, wherein $R^6$ is a monovalent hydrocarbon group having from 1 to 20 carbon atoms, and —OSi containing groups that result from the condensation of silanols;

each occurrence of the subscripts, a, b, c, d, e, m, n, o, p, and x, is independently given wherein a, c and e are 1 to about 3; b is 1 to about 5; d is 1 to about 5; m and p are 1 to about 100; n is 1 to about 15; o is 0 to about 10; and x is 1 to about 10.

2. The silated cyclic core polysulfide of claim 1 wherein $R^1$ and $R^3$ are branched or straight chain alkyl, alkenyl, alkynyl, aryl or aralkyl groups in which one hydrogen atom is substituted with a $Y^1$ or $Y^2$ group.

3. The silated cyclic core polysulfide of claim 1 wherein $R^6$ is branched or straight chain alkyl, alkenyl, aryl or aralkyl.

4. The silated cyclic core polysulfide of claim 1 wherein $R^4$ is cyclic or polycyclic alkyl, alkenyl, alkynyl, aryl, or aralkyl in which a+c+e−1 hydrogens have been replaced.

5. The silated cyclic core polysulfide of claim 1 wherein $R^4$ and $R^5$ are polyvalent heterocarbon fragments from 3 to 27 carbon atoms.

6. The silated cyclic core polysulfide of claim 1 wherein $R^5$ is cyclic or polycyclic alkyl, alkenyl, alkynyl, aryl, or aralkyl in which a+c+e−1 hydrogens have been replaced.

7. The silated cyclic core polysulfide of claim 6 wherein the heteroatom of $R^4$ and $R^5$ is selected from the group consisting of sulfur, oxygen, nitrogen, and mixture thereof.

8. The silated cyclic core polysulfide of claim 1 wherein the cyclic or polycyclic alkyl, alkynyl, aryl, aralkyl and arenyl of $R_4$ in which a+c+e−1hydrogens have been replaced is selected from the group consisting of ethylidenyl norbornane, ethylidene norbornyl, ethylidenyl norbornene, ethylidene norbornenyl, phenyl, naphthalenyl, benzyl, phenethyl, tolyl, xylyl, norbornyl, norbornenyl, ethylnorbornyl, ethylnorbornenyl, cyclohexyl, ethylcyclohexyl, ethylcyclohexenyl, cyclohexylcyclohexyl, and cyclododecatrienyl.

9. The silated cyclic core polysulfide of claim 1 wherein the cyclic alkyl, alkynyl, aryl, aralkyl and arenyl of $R^5$ in which c+e−1 hydrogens have been replaced is selected from the group consisting of ethylidenyl norbornane, ethylidene norbornyl, ethylidenyl norbornene, ethylidene norbornenyl, phenyl, naphthalenyl, benzyl, phenethyl, tolyl, xylyl, norbornyl, norbornenyl, ethylnorbornyl, ethylnorbornenyl, cyclohexyl, ethylcyclohexyl, ethylcyclohexenyl, cyclohexylcyclohexyl, and cyclododecatrienyl.

10. The silated cyclic core polysulfide of claim 1 wherein cyclic structure of $R^4$, $R^5$, and $R^6$ is selected from the group consisting of bicyclic, tricyclic, higher cyclic structures, cyclic structures substituted with alkyl, alkenyl, and/or alkynyl groups.

11. The silated cyclic core polysulfide of claim 1 wherein $X^1$ is selected from the group of methoxy, ethoxy, propoxy, isopropoxy, butoxy, phenoxy, benzyloxy, hydroxy, chloro, and acetoxy.

12. The silated cyclic core polysulfide of claim 1 wherein $X^2$ and $X^3$ are selected from the group consisting of methoxy, ethoxy, propoxy, isopropoxy, butoxy, phenoxy, benzyloxy, hydroxy, chloro, acetoxy, hydrogen, methyl, ethyl, propyl, isopropyl, sec-butyl, phenyl, vinyl, cyclohexyl, straight-chain alkyl, butyl, hexyl, octyl, lauryl, and octadecyl.

13. The silated cyclic core polysulfide of claim 1 wherein $R^1$ and $R^3$ are terminal straight-chain alkyls substituted terminally at the end with —$CH_2$—, —$CH_2CH_2$—, —$CH_2CH_2CH_2$—, —$CH_2CH_2CH_2CH_2CH_2CH_2CH_2CH_2$—, beta-substituted analogs, and mixtures thereof.

14. The silated cyclic core polysulfide of claim 13 wherein the beta substituted analog is —$CH_2(CH_2)_uCH(CH_3)$—, where u is zero to 17.

15. The silated cyclic core polysulfide of claim 13 wherein $R^1$ and $R^3$ are structures derived from methallyl chloride, divinylbenzene, diallylether, butadiene, piperylene, isoprene, diradicals, limonene, monovinyl-containing structures derived from trivinylcyclohexane, monounsaturated structures derived from myrcene containing a trisubstituted C=C, monounsaturated structures derived from myrcene lacking a trisubstituted C=C, and mixtures thereof.

16. The silated cyclic core polysulfide of claim 1 wherein $G^1$ is selected from the group consisting of structures derivable from divinylbenzene, such as —$CH_2CH_2(C_6H_4)CH(CH_2$—)— and —$CH_2CH_2(C_6H_3$—)$CH_2CH_2$—, —$CH_2(CH$—)$(C_6H_4)CH(CH_2$—)—, where the notation $C_6H_4$ denotes a disubstituted benzene ring and $C_6H_3$— denotes a trisubstituted ring.

17. The silated cyclic core polysulfide of claim 1 wherein $G^1$ is derived from trivinylcyclohexane, such as —$CH_2(CH$—)(vinyl$C_6H_9)CH_2CH_2$—; (—$CH_2CH_2)_3C_6H_9$, and (—$CH_2CH_2)_2C_6H_9CH(CH_3)$—, —$CH_2(CH$—)(vinyl$C_6H_9)(CH$—)$CH_2$—, —$CH_2CH_2C_6H_9[(CH$—)$CH_2$—$]_2$, —$CH(CH_3)C_6H_9[(CH$—)$CH_2$—$]_2$, and $C_6H_9[(CH$—)$CH_2$—$]_3$, —$CH_2(CH$—)$C_6H_9[CH_2CH_2$—$]_2$, and —$CH_2(CH$—)$C_6H_9[CH(CH_3)$—][$CH_2CH_2$—], where the notation $C_6H_9$ denotes any isomer of the trisubstituted cyclohexane ring.

18. The silated cyclic core polysulfide of claim 1 wherein $G^2$ is derived from divinylbenzene, such as —$CH_2CH_2(C_6H_4)CH_2CH_2$—, —$CH_2CH_2(C_6H_4)CH(CH_2$—)— and —$CH_2CH_2(C_6H_3$—)$CH_2CH_2$—, —$CH_2(CH$—)$(C_6H_4)CH(CH_2$—)—, where the notation $C_6H_4$ denotes a disubstituted benzene ring.

19. The silated cyclic core polysulfide of claim 1 wherein $G^2$ is selected from —$CH_2CH_2$(vinyl$C_6H_9)CH_2CH_2$—, (—$CH_2CH_2)C_6H_9CH_2CH_3$, —$CH_2(CH$—)(vinyl$C_6H_9)CH_2CH_2$—, (—$CH_2CH_2)_3C_6H_9$, (—$CH_2CH_2)_2C_6H_9CH(CH_3)$—, —$CH_2(CH$—)(vinyl$C_6H_9)(CH$—)$CH_2$—, —$CH_2CH_2C_6H_9[(CH$—)$CH_2$—$]_2$, —$CH(CH_3)C_6H_9[(CH$—)$CH_2$—$]_2$, and $C_6H_9[(CH$—)$CH_2$—$]_3$, —$CH_2(CH$—)$C_6H_9[CH_2CH_2$—$]_2$, and —$CH_2(CH$—)$C_6H_9[CH(CH_3)$—][$CH_2CH_2$—], where the notation $C_6H_9$ denotes any isomer of the trisubstituted cyclohexane ring.

20. The silated cyclic core polysulfide of claim 1 wherein the silated cyclic core polysulfide is any of the isomers of 4-(6-triethoxysilyl-3-thiahexyl) -1,2-bis-(13-triethoxysilyl-3,4,5,6-tetrathiamidecyl)cyclohexane; 4-(6-triethoxysilyl-3-thiahexyl) -1,2-bis-(13-triethoxysilyl-3,4-dithiamidecyl)cyclohexane; 4-(6-triethoxysilyl-3-thiahexyl) -1,2-bis-(13-triethoxysilyl-3,4,5-trithiamidecyl)cyclohexane; 4-(6-triethoxysilyl-3-thiahexyl) -1,2-bis-(12-triethoxysilyl-3,4,5-tetrathiadodecyl)cyclohexane; 1-(6-triethoxysilyl-3-thiahexyl) -2,4-bis-(11-triethoxysilyl-3,4-tetrathiaunidecyl) cyclohexane 4-(3-triethoxysilyl-1-thiaethyl) -1,2-bis-(13-triethoxysilyl-3,4,5,6,7-pentathiamidecyl)cyclohexane;

4-(6-diethoxymethylsilyl-2-thia hexyl)-1,2-bis-(13-triethoxysilyl-3,4,5,6-tetrathiatridecyl)cyclohexane; 4-(4-triethoxysilyl-2-thiabutyl)-1,2-bis-(9-triethoxysilyl-3,4,5,6-tetrathianonyl)cyclohexane; 4-(7-triethoxysilyl-3-thiaheptyl)-1,2-bis-(9-triethoxysilyl-3,4,5-trithianonyl) cyclohexane; 4-(5-triethoxysilyl-2-thiapentyl)-1,2-bis-(9-triethoxysilyl-3,4,5,6-tetrathianonyl)benzene; 4-(5-triethoxysilyl-2-thiapentyl)-1,2-bis-(9-triethoxysilyl-3,4,5-trithianonyl)benzene; 4-(5-triethoxysilyl-2-thiapentyl)-1,2-bis-(9-triethoxysilyl-3,4-dithianonyl)benzene; bis-2-[4-(3-triethoxysilyl-2-thiapropyl)-3-(9-triethoxysilyl-3,4,5,6-tetrathianonyl)cyclohexyl]ethyl tetrasulfide; bis-2-[4-(3-triethoxysilyl-1-thiapropyl)-3-(9-triethoxysilyl -3,4,5,6-tetrathianonyl)cyclohexyl]ethyl trisulfide; bis-2-[4-(3-triethoxysilyl-1-thiapropyl) -3-(7-triethoxysilyl-3,4-dithiaheptyl)cyclohexyl]ethyl disulfide; bis-2-[4-(6-triethoxysilyl -3-thiahexyl)-3-(9-triethoxysilyl-3,4,5-trithianonyl)phenyl]ethyl tetrasulfide; bis-2-[4-(6-triethoxysilyl-3-thiahexyl)-3-(9-triethoxysilyl-3,4,5-trithianonyl)nathyl]ethyl tetrasulfide; bis-2-[4-(4-diethoxymethylsilyl-2-thiabutyl)-3-(9-triethoxysilyl-3,4,5,6-tetrathianonyl)phenyl]ethyl trisulfide; bis-2-[4-(4-triethoxysilyl-2-thiaethyl)-3-(7-triethoxysilyl -3,4-dithiaheptyl)cycloheptyl]ethyl disulfide; bis-2-[4-(4-triethoxysilyl-2-thiaethyl)-3-(7-triethoxysilyl -3,4-dithiaheptyl)cyclooctyl]ethyl disulfide; bis-2-[4-(4-triethoxysilyl-2-thiaethyl) -3-(7-triethoxysilyl-3,4-dithiaheptyl)cyclododecyl]ethyl disulfide; 4-(6-triethoxysilyl-3-thiahexyl) -1,2-bis-(9-triethoxysilyl-3,4,5,6-tetrathianonyl)cyclohexane; 2-(6-triethoxysilyl-3-thiahexyl) -1,4-bis-(9-triethoxysilyl-3,4,5,6-tetrathianonyl)cyclohexane; 1-(6-triethoxysilyl-3-thiahexyl) -2,4-bis-(9-triethoxysilyl-3,4,5,6-tetrathianonyl)cyclohexane; 4-(6-triethoxysilyl-3-thiahexyl) -1,2-bis-(7-triethoxysilyl-3,4-dithiaheptyl)cyclohexane; 2-(6-triethoxysilyl-3-thiahexyl) -1,4-bis-(7-triethoxysilyl-3,4-dithiaheptyl)cyclohexane; 1-(6-triethoxysilyl-3-thiahexyl) -2,4-bis-(7-triethoxysilyl-3,4-dithiaheptyl)cyclohexane, and mixtures thereof.

21. The silated cyclic core polysulfide of claim 1 wherein $R^1$ and $R^3$ are independently selected from a divalent hydrocarbon fragment having from 1 to about 5 carbon atoms.

22. The silated cyclic core polysulfide of claim 21 wherein $R^1$ and $R^3$ are that are branched and/or straight chain alkyl, alkenyl or alkynyl groups in which one hydrogen atom was substituted with a $Y^1$ or $Y^2$ group.

23. The silated cyclic core polysulfide of claim 21 wherein $Y^1$ and $Y^2$ are silyl ($-SiX^1$, $X^2$, $X^3$), hydrogen, alkoxy ($-OR^6$), carboxylic acid, ester ($-C(=O)OR^6$) wherein $R^6$ is a monohydrocarbon group having from 1 to 5 carbon atoms.

24. The silated cyclic core polysulfide of claim 21 wherein $R^2$ is a straight chain hydrocarbon represented by $-(CH_2)_f-$ where f is an integer from about 1 to about 5.

25. The silated cyclic core polysulfide of claim 21 wherein $R^4$ is a polyvalent hydrocarbon fragment of 5 to about 12 carbon atoms.

26. The silated cyclic core polysulfide of claim 21 wherein $R^5$ is a polyvalent hydrocarbon fragment of 5 to about 12 carbon atoms.

27. The silated cyclic core polysulfide of claim 21 wherein $X^1$ is independently selected from the group consisting of hydrolysable $-OH$, and $-OR^6$, wherein $R^6$ is a monovalent hydrocarbon group having from 1 to 5 carbon atoms.

28. The silated cyclic core polysulfide of claim 27 wherein each occurrence of the subscripts, a, b, c, d, e, f, m, n, o, p, and x, is independently given by a is 1 to about 2; b and d are 1 to about 3; c and e are 1; f is 1 to about 5; m and p are 1, n is 1 to about 10; o is 0 to about 1; and x is 1 to about 6.

29. The silated cyclic core polysulfide of claim 21 wherein $X^2$ and $X^3$ are independently selected from the group consisting of $R^6$, wherein $R^6$ is a monovalent hydrocarbon group having from 1 to 5 carbon atoms, $X^1$, wherein $X^1$ is independently selected from the group consisting of hydrolysable $-OH$, $-OR^6$, wherein $R^6$ is a monovalent hydrocarbon group having from 1 to 5 carbon atoms, and $-OSi$ containing groups that result from the condensation of silanols.

30. A process for making a silated cyclic core polysulfide according to claim 1 which comprises:
   a) reacting a thioacid with the structure, $R^6C(=O)SH$ with a hydrocarbon containing reactive double bonds;
   b) deblocking the mercapto group using a proton donator;
   c) reacting the intermediate mercaptan in step b with a base and then a halo containing hydrocarbon silane;
   (d) reacting the intermediate mercapto silane from step c with a base and sulfur;
   (e) reacting the intermediate in step d with a substituted or unsubstituted hydrocarbon containing a leaving group selected from chlorine, bromine or iodine, and mixtures thereof.

31. The process of claim 30 wherein $R^6$ is a monovalent hydrocarbon group from 1 to 20 carbon atoms.

32. The process of claim 30 wherein the process is carried out in an organic solvent.

33. The process of claim 32 wherein the organic solvent is selected from the group consisting of ethanol, methanol, isopropyl alcohol, tetrahydrofuran, diethyl ether, hexanes, cyclohexane, toluene, xylenes, and mixtures thereof.

34. The process of claim 30 wherein the hydrocarbon containing at least one double bond in step (a) has the general formula:

wherein $R^4$ is independently selected from a polyvalent hydrocarbon fragment of 1 to about 28 carbon atoms and the subscripts g, h and i are about 0 to 3.

35. The process of claim 30 wherein the free radical agent of step (b) is an oxidizing agent that converts thiocarboxylic acid to a thiocarboxylic acid radical.

36. The process of claim 35 wherein the oxidizing agent is selected from the group consisting of oxygen, peroxides, hydroperoxides, and mixtures thereof.

37. The process of claim 36 wherein the proton donator of step (c) is a hydrogen containing heterocarbon or substituted heterocarbon that is capable of reacting with the intermediate of step (b).

38. The process of claim 30 wherein the proton donor is selected from the group consisting of alcohols, amines, mercaptans, and mixtures thereof.

39. The process of claim 38 wherein the alcohol is selected from the group consisting of methanol, ethanol, isopropyl alcohol, propanol, and mixtures thereof.

40. The process of claim 38 wherein the amine is selected from the group consisting of ammonia, methyl amine, propyl amine, diethanol amine, and mixtures thereof.

41. The process of claim 38 wherein the mercaptan is selected from the group consisting of propyl mercaptans, butyl mercaptan, and mixtures thereof.

42. The process of claim 30 wherein the substituted or unsubstituted hydrocarbon of step (e) has the general formulae selected from the group consisting of:

$Y^1R^1Z$; or $Y^2R^3Z$;

wherein each occurrence of $Y^1$ and $Y^2$, are independently selected from the group consisting of silyl (—$SiX^1X^2X^3$), hydrogen, alkoxy (—$OR^6$), carboxylic acid, ester (—C(=O)$OR^6$) wherein $R^6$ is a monovalent hydrocarbon group having from 1 to 20 carbon atoms, $R^1$, and $R^3$ are independently selected from a divalent hydrocarbon fragment having from 1 to about 20 carbon atoms, and Z is selected from the group consisting of Cl, Br and I, and mixtures thereof.

43. The process of claim 30 wherein the silated cyclic core polysulfide is any of the isomers of 4-(6-triethoxysilyl-3-thiahexyl)-1,2-bis -13-triethoxysilyl-3,4,5,6-tetrathiamidecyl)cyclohexane; 4-(6-triethoxysilyl-3-thiahexyl)-1,2-bis -13-triethoxysilyl-3,4-dithiamidecyl)cyclohexane; 4-(6-triethoxysilyl-3-thiahexyl)-1,2-bis-(13-triethoxysilyl -3,4,5-trithiamidecyl)cyclohexane; 4-(6-triethoxysilyl-3-thiahexyl)-1,2-bis-(12-triethoxysilyl -3,4,5-tetrathiadodecyl) cyclohexane; 1-(6-triethoxysilyl-3-thiahexyl)-2,4-bis-(11-triethoxysilyl -3,4-tetrathiaunidecyl)cyclohexane 4-(3-triethoxysilyl-1-thiaethyl)-1,2-bis-(13-triethoxysilyl -3,4,5,6,7-pentathiamidecyl)cyclohexane; 4-(6-diethoxymethylsilyl-2-thia hexyl) -1,2-bis-(13-triethoxysilyl-3,4,5,6-tetrathiamidecyl)cyclohexane; 4-(4-triethoxysilyl-2-thiabutyl) -1,2-bis-(9-triethoxysilyl-3,4,5,6-tetrathianonyl)cyclohexane; 4-(7-triethoxysilyl-3-thiaheptyl) -1,2-bis-(9-triethoxysilyl-3,4,5-trithianonyl)cyclohexane; 4-(5-triethoxysilyl-2-thiapentyl)-1,2-bis -9-triethoxysilyl-3,4,5,6-tetrathianonyl)benzene; 4-(5-triethoxysilyl-2-thiapentyl)-1,2-bis-(9-triethoxysilyl -3,4,5-trithianonyl)benzene; 4-(5-triethoxysilyl-2-thiapentyl)-1,2-bis-(9-triethoxysilyl -3,4-dithianonyl)benzene; bis-2-[4-(3-triethoxysilyl-2-thiapropyl)-3-(9-triethoxysilyl -3,4,5,6-tetrathianonyl)cyclohexyl]ethyl tetrasulfide; bis-2-[4-(3-triethoxysilyl-1-thiapropyl) -3-(9-triethoxysilyl-3,4,5,6-tetrathianonyl)cyclohexyl]ethyl trisulfide; bis-2-[4-(3-triethoxysilyl -1-thiapropyl)-3-(7-triethoxysilyl-3,4-dithiaheptyl)cyclohexyl]ethyl disulfide; bis-2-[4-(6-triethoxysilyl-3-thiahexyl)-3-(9-triethoxysilyl-3,4,5-trithianonyl)phenyl]ethyl tetrasulfide; bis-2-[4-(6-triethoxysilyl-3-thiahexyl)-3-(9-triethoxysilyl-3,4,5-trithianonyl)nathyl]ethyl tetrasulfide; bis-2-[4-(4-diethoxymethylsilyl-2-thiabutyl)-3-(9-triethoxysilyl-3,4,5,6-tetrathianonyl)phenyl]ethyl trisulfide; bis-2-[4-(4-triethoxysilyl-2-thiaethyl)-3-(7-triethoxysilyl -3,4-dithiaheptyl)cycloheptyl]ethyl disulfide; bis-2-[4-(4-triethoxysilyl-2-thiaethyl)-3-(7-triethoxysilyl -3,4-dithiaheptyl)cyclooctyl]ethyl disulfide; bis-2-[4-(4-triethoxysilyl-2-thiaethyl) -3-(7-triethoxysilyl-3,4-dithiaheptyl)cyclododecyl]ethyl disulfide; 4-(6-triethoxysilyl-3-thiahexyl) -1,2-bis-(9-triethoxysilyl-3,4,5,6-tetrathianonyl)cyclohexane; 2-(6-triethoxysilyl-3-thiahexyl) -1,4-bis-(9-triethoxysilyl-3,4,5,6-tetrathianonyl) cyclohexane; 1-(6-triethoxysilyl-3-thiahexyl) -2,4-bis-(9-triethoxysilyl-3,4,5,6-tetrathianonyl)cyclohexane; 4-(6-triethoxysilyl-3-thiahexyl) -1,2-bis-(7-triethoxysilyl-3,4-dithiaheptyl)cyclohexane; 2-(6-triethoxysilyl-3-thiahexyl) -1,4-bis-(7-triethoxysilyl-3,4-dithiaheptyl)cyclohexane; 1-(6-triethoxysilyl-3-thiahexyl) -2,4-bis-(7-triethoxysilyl-3,4-dithiaheptyl)cyclohexane, and mixtures thereof.

44. A rubber composition comprising:
a) silated cyclic core polysulfide of the general formula $[Y^1R^1S_x—]_m[G^1(SR^2SiX^1X^2X^3)_a]_n[G^2]_o[R^3Y^2]_p$;

wherein each occurrence of $G^1$ is independently selected from a polyvalent hydrocarbon or heterocarbon species having from 5 to about 30 carbon atoms containing a polysulfide group represented by the general formula:

$[(CH_2)_b—]_cR^4[—(CH_2)_dS_x—]_e$;

each occurrence of $G^2$ is independently selected from a polyvalent hydrocarbon or heterocarbon species of 3 to about 30 carbon atoms containing a polysulfide group represented by the general formula:

$[(CH_2)_b—]_cR^5[—(CH_2)_dS_x—]_e$;

each occurrence of $R^1$ and $R^3$ is independently selected from a divalent hydrocarbon fragment having from 1 to about 20 carbon atoms;

each occurrence of $Y^1$ and $Y^2$ is independently selected from consisting of silyl (—$SiX^1X^2X^3$), alkoxy (—$OR^6$), hydrogen, carboxylic acid, ester (—C(=O)$OR^6$) wherein $R^6$ is a monovalent hydrocarbon group having from 1 to 20 carbon atoms;

each occurrence of $R^2$ is independently selected from a divalent hydrocarbon fragment having from 1 to about 20 carbon atoms that include branched and straight chain alkyl, alkenyl, alkynyl, aryl or aralkyl;

each occurrence of $R^4$ is independently selected from a polyvalent cyclic hydrocarbon fragment of 3 to about 28 carbon atoms or a polyvalent cyclic heterocarbon fragment of 3 to about 27 carbon atoms that was obtained by substitution of hydrogen atoms equal to the sum of a+c+e;

each occurrence of $R^5$ is chosen independently from a polyvalent hydrocarbon fragment of 1 to about 28 carbon atoms or a polyvalent cyclic heterocarbon fragment of 1 to about 27 carbon atoms that was obtained by substitution of hydrogen atoms equal to the sum of c+e;

each occurrence of $X^1$ is independently selected from the group consisting of —Cl, —Br, —OH, —$OR^6$, and $R^6$C(=O)O—, wherein $R^6$ is a monovalent hydrocarbon group having from 1 to 20 carbon atoms;

each occurrence of $X^2$ and $X^3$ is independently selected from the group consisting of hydrogen, $R^6$, wherein $R^6$ is a monovalent hydrocarbon group having from 1 to 20 carbon atoms, $X^1$, wherein $X^1$ is independently selected from the group consisting of —Cl, —Br, —OH, —$OR^6$, and $R^6$C(=O)O—, wherein $R^6$ is a monovalent hydrocarbon group having from 1 to 20 carbon atoms, and —OSi containing groups that result from the condensation of silanols;

each occurrence of the subscripts, a, b, c, d, e, m, n, o, p, and x, is independently given by a, c and e are 1 to about 3; b is 1 to about 5; d is 1 to about 5; m and p are 1 to about 100; n is 1 to about 15; o is 0 to about 10; and x is 1 to about 10;

(b) inorganic filler; and,
(c) rubber.

45. The rubber composition of claim 44, further comprising (d) curative and, optionally, at least one other additive selected from the group consisting of sulfur compounds, activators, retarders, accelerators, processing additives, oils, plasticizers, tackifying resins, silicas, fillers, pigments, fatty acids, zinc oxide, waxes, antioxidants and antiozonants, peptizing agents, reinforcing materials, and mixtures thereof.

46. The rubber composition of claim 44, wherein the rubber component is at least one sulfur vulcanizable rubber selected from the group consisting of conjugated diene homopolymers and copolymers, copolymers of at least one conjugated diene and aromatic vinyl compound and mixtures thereof.

47. The rubber composition of claim 46, wherein the conjugated dienes is selected from the group consisting of isoprene, 1,3-butadiene, styrene, and alpha methyl styrene, and mixture thereof.

48. The rubber composition of claim 44, wherein the rubber component is at least one natural rubber.

49. The rubber composition of claim 44, wherein the rubber component is at least one emulsion polymerization derived rubber.

50. The rubber composition of claim 49, wherein the emulsion polymerization derived rubber is at least one such rubber selected from the group consisting of styrene/butadiene rubber, emulsion-prepared styrene-butadiene rubber, ethylene-propylene copolymers and terpolymer, butadiene/acrylonitrile rubber, polybutadiene rubber and styrene/butadiene/acrylonitrile rubber.

51. The rubber composition of claim 50 wherein the emulsion polymerization prepared styrene/butadiene/acrylonitrile terpolymer rubber contains from about 2 to about 40 weight percent acrylonitrile.

52. The rubber composition of claim 44, wherein the rubber component is at least one solvent polymerization derived rubber.

53. The rubber composition of claim 52, wherein the solvent polymerization derived rubber is styrene/butadiene rubber containing from about 5 to about 50 percent vinyl content.

54. The rubber composition of claim 53, wherein the solvent polymerization derived rubber is styrene/butadiene rubber containing from about 9 to about 36 percent vinyl content.

55. The rubber composition of claim 44, wherein the rubber is a polybutadiene where about 90 weight percent is in the cis-1,4-butadiene form.

56. The rubber composition of claim 44, wherein the rubber is selected from the group consisting of cis-1,4-polyisoprene rubber, emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber, wherein the medium vinyl polybutadiene rubber has about 35 to 50 weight percent vinyl, high vinyl polybutadiene rubber wherein the high vinyl polybutadiene rubber has about 50 to 75 weight percent vinyl, styrene/isoprene copolymers, emulsion polymerization prepared styrene/butadiene/acrylonitrile terpolymer rubber and butadiene/acrylonitrile copolymer rubber.

57. The rubber composition of claim 56 wherein the emulsion polymerization derived styrene/butadiene copolymer rubber has a styrene content of about 20 to about 28 weight percent.

58. The rubber composition of claim 56 wherein the emulsion polymerization derived styrene/butadiene copolymer rubber has a styrene content of about 30 to about 45 weight percent.

59. The rubber composition of claim 44, wherein the silated cyclic core polysulfide is any of the isomers of 4-(6-triethoxysilyl-3-thiahexyl)-1,2-bis -13-triethoxysilyl-3,4,5,6-tetrathiamidecyl)cyclohexane; 4-(6-triethoxysilyl-3-thiahexyl)-1,2-bis -(13-triethoxysilyl-3,4-dithiamidecyl)cyclohexane; 4-(6-triethoxysilyl-3-thiahexyl)-1,2-bis-(13-triethoxysilyl -3,4,5-trithiamidecyl)cyclohexane; 4-(6-triethoxysilyl-3-thiahexyl)-1,2-bis-(12-triethoxysilyl -3,4,5-tetrathiadodecyl)cyclohexane; 1-(6-triethoxysilyl-3-thiahexyl)-2,4-bis-(11-triethoxysilyl -3,4-tetrathiaunidecyl)cyclohexane 4-(3-triethoxysilyl-1-thiaethyl)-1,2-bis-(13-triethoxysilyl -3,4,5,6,7-pentathiamidecyl)cyclohexane; 4-(6-diethoxymethylsilyl-2-thia hexyl) -1,2-bis-(13-triethoxysilyl-3,4,5,6-tetrathiatridecyl)cyclohexane; 4-(4-triethoxysilyl-2-thiabutyl) -1,2-bis-(9-triethoxysilyl-3,4,5,6-tetrathianonyl)cyclohexane; 4-(7-triethoxysilyl-3-thiaheptyl) -1,2-bis-(9-triethoxysilyl-3,4,5-trithianonyl)cyclohexane; 4-(5-triethoxysilyl-2-thiapentyl)-1,2-bis -9-triethoxysilyl-3,4,5,6-tetrathianonyl)benzene; 4-(5-triethoxysilyl-2-thiapentyl)-1,2-bis-(9-triethoxysilyl -3,4,5-trithianonyl)benzene; 4-(5-triethoxysilyl-2-thiapentyl)-1,2-bis-(9-triethoxysilyl -3,4-dithianonyl)benzene; bis-2-[4-(3-triethoxysilyl-2-thiapropyl)-3-(9-triethoxysilyl -3,4,5,6-tetrathianonyl)cyclohexyl]ethyl tetrasulfide; bis-2-[4-(3-triethoxysilyl-1-thiapropyl) -3-(9-triethoxysilyl-3,4,5,6-tetrathianonyl)cyclohexyl]ethyl trisulfide; bis-2-[4-(3-triethoxysilyl -1-thiapropyl)-3-(7-triethoxysilyl-3,4-dithiaheptyl)cyclohexyl]ethyl disulfide; bis-2-[4-(6-triethoxysilyl-3-thiahexyl)-3-(9-triethoxysilyl-3,4,5-trithianonyl)phenyl]ethyl tetrasulfide; bis-2-[4-(6-triethoxysilyl-3-thiahexyl)-3-(9-triethoxysilyl-3,4,5-trithianonyl)nathyl]ethyl tetrasulfide; bis-2-[4-(4-diethoxymethylsilyl-2-thiabutyl)-3-(9-triethoxysilyl-3,4,5,6-tetrathianonyl)phenyl]ethyl trisulfide; bis-2-[4-(4-triethoxysilyl-2-thiaethyl)-3-(7-triethoxysilyl -3,4-dithiaheptyl)cycloheptyl]ethyl disulfide; bis-2-[4-(4-triethoxysilyl-2-thiaethyl)-3-(7-triethoxysilyl -3,4-dithiaheptyl)cyclooctyl]ethyl disulfide; bis-2-[4-(4-triethoxysilyl-2-thiaethyl) -3-(7-triethoxysilyl-3,4-dithiaheptyl)cyclododecyl]ethyl disulfide; 4-(6-triethoxysilyl-3-thiahexyl) -1,2-bis-(9-triethoxysilyl-3,4,5,6-tetrathianonyl)cyclohexane; 2-(6-triethoxysilyl-3-thiahexyl) -1,4-bis-(9-triethoxysilyl-3,4,5,6-tetrathianonyl)cyclohexane; 1-(6-triethoxysilyl-3-thiahexyl) -2,4-bis-(9-triethoxysilyl-3,4,5,6-tetrathianonyl)cyclohexane; 4-(6-triethoxysilyl-3-thiahexyl) -1,2-bis-(7-triethoxysilyl-3,4-dithiaheptyl)cyclohexane; 2-(6-triethoxysilyl-3-thiahexyl) -1,4-bis-(7-triethoxysilyl-3,4-dithiaheptyl)cyclohexane; 1-(6-triethoxysilyl-3-thiahexyl) -2,4-bis-(7-triethoxysilyl-3,4-dithiaheptyl)cyclohexane, and mixtures thereof.

60. The rubber composition of claim 44 wherein the total amount of silated cyclic core polysulfide present in the rubber composition is from about 0.05 to about 25 parts by weight per hundred parts by weight of rubber.

61. The rubber composition of claim 44 wherein the total amount of silated cyclic core polysulfide present in the rubber composition is from about 1 to about 10 parts by weight per hundred parts by weight of rubber.

62. The rubber composition of claim 61 wherein the filler is from about 5 to about 100 parts by weight per hundred parts.

63. The rubber composition of claim 61 wherein the filler is from about 25 to about 80 parts by weight per hundred parts.

* * * * *